(12) United States Patent
Kamon

(10) Patent No.: US 11,684,237 B2
(45) Date of Patent: Jun. 27, 2023

(54) ENDOSCOPIC IMAGE ACQUISITION SYSTEM AND METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 134 days.

(21) Appl. No.: 16/901,022

(22) Filed: Jun. 15, 2020

(65) Prior Publication Data

US 2020/0305700 A1    Oct. 1, 2020

Related U.S. Application Data

(63) Continuation of application No. PCT/JP2018/043790, filed on Nov. 28, 2018.

(30) Foreign Application Priority Data

Dec. 28, 2017   (JP) .................................. 2017-254275

(51) Int. Cl.
*A61B 1/00* (2006.01)
*A61B 1/06* (2006.01)

(52) U.S. Cl.
CPC ........ *A61B 1/00006* (2013.01); *A61B 1/0005* (2013.01); *A61B 1/00042* (2022.02);
(Continued)

(58) Field of Classification Search
CPC .................................................. A61B 1/0646
See application file for complete search history.

(56) References Cited

U.S. PATENT DOCUMENTS 5,078,150 A * 1/1992 Hara .................... H04N 5/2256
600/478
8,723,937 B2  5/2014 Sasaki
(Continued)

FOREIGN PATENT DOCUMENTS

CN   102188219    9/2011
CN   102197983    9/2011
(Continued)

OTHER PUBLICATIONS

"Office Action of Japan Counterpart Application" with English translation thereof, dated Jun. 4, 2021, p. 1-p. 13.
(Continued)

*Primary Examiner* — John P Leubecker
*Assistant Examiner* — Jae Woo
(74) *Attorney, Agent, or Firm* — JCIPRNET

(57) ABSTRACT

Provided are endoscopic image acquisition system and method that make observation of images easier when images are collected. The endoscopic image acquisition system includes a wavelength pattern changing unit that changes a wavelength pattern of irradiation light with which a part to be observed in a body cavity of a patient is irradiated or returning light from the part to be observed. Images of an observation wavelength pattern are captured at a certain frame rate. In response to acceptance of an acquisition instruction, images of a plurality of wavelength patterns different from one another are sequentially captured. The images of the plurality of wavelength patterns different from one another are stored in a storage unit. An image of a wavelength pattern other than the observation wavelength pattern is set not to be displayed.

16 Claims, 15 Drawing Sheets

(52) U.S. Cl.
CPC ...... *A61B 1/000094* (2022.02); *A61B 1/0638* (2013.01); *A61B 1/0646* (2013.01); *A61B 1/0655* (2022.02)

(56) References Cited

U.S. PATENT DOCUMENTS

| | | | | |
|---|---|---|---|---|
| 2002/0175993 | A1* | 11/2002 | Ueno | A61B 5/0084 348/68 |
| 2008/0091065 | A1* | 4/2008 | Oshima | H04N 19/60 382/128 |
| 2008/0304724 | A1* | 12/2008 | Eino | A61B 1/00022 382/128 |
| 2011/0178395 | A1* | 7/2011 | Miesner | A61B 5/6855 600/425 |
| 2011/0237883 | A1* | 9/2011 | Chun | A61B 1/0638 600/109 |
| 2013/0245411 | A1* | 9/2013 | Saito | A61B 1/0051 600/339 |
| 2019/0087970 | A1* | 3/2019 | Endo | A61B 5/489 |

FOREIGN PATENT DOCUMENTS

| | | |
|---|---|---|
| CN | 102266217 | 12/2011 |
| EP | 2368485 | 9/2011 |
| JP | 2001170009 | 6/2001 |
| JP | 2010172673 | 8/2010 |
| JP | 2011200517 | 10/2011 |
| JP | 2011250926 | 12/2011 |
| JP | 2013188364 | 9/2013 |
| JP | 2015042193 | 3/2015 |
| JP | 2016202411 | 12/2016 |
| WO | 2017183324 | 10/2017 |

OTHER PUBLICATIONS

"International Search Report (Form PCT/ISA/210)" of PCT/JP2018/043790, dated Feb. 12, 2019, with English translation thereof, pp. 1-5.

"Written Opinion of the International Searching Authority (Form PCT/ISA/237)" of PCT/JP2018/043790, dated Feb. 12, 2019, with English translation thereof, pp. 1-14.

"Office Action of Japan Counterpart Application" with English translation thereof, dated Feb. 19, 2021, p. 1-p. 8.

"Search Report of Europe Counterpart Application", dated Feb. 8, 2021, p. 1-p. 8.

"Office Action of China Counterpart Application", dated Feb. 25, 2023, with English translation thereof, p. 1-p. 13.

* cited by examiner

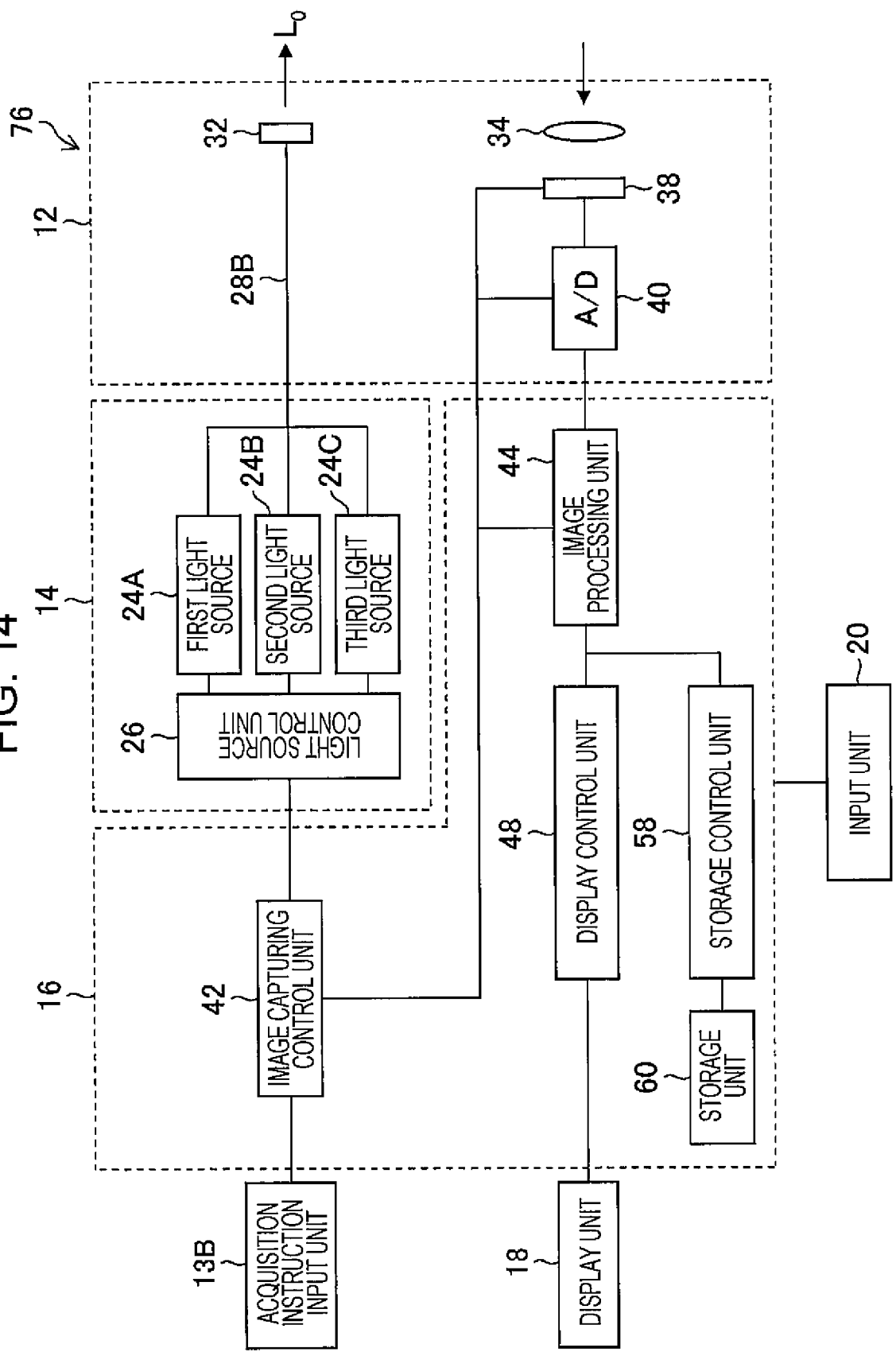

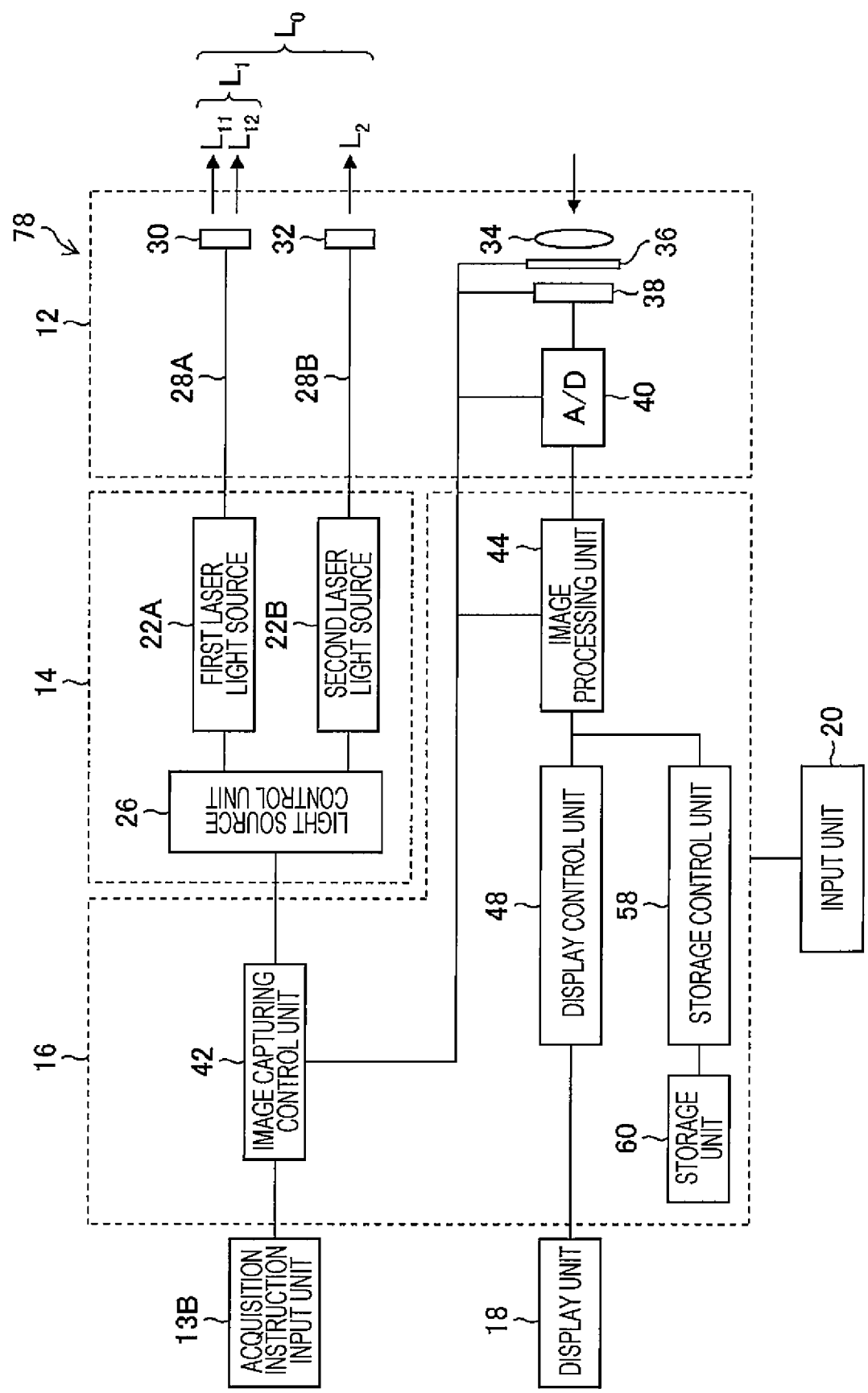

ENDOSCOPIC IMAGE ACQUISITION SYSTEM AND METHOD

CROSS-REFERENCE TO RELATED APPLICATIONS

The present application is a Continuation of PCT International Application No. PCT/JP2018/043790 filed on Nov. 28, 2018 claiming priority under 35 U.S.C. § 119(a) to Japanese Patent Application No. 2017-254275 filed on Dec. 28, 2017. Each of the above applications is hereby expressly incorporated by reference, in its entirety, into the present application.

BACKGROUND OF THE INVENTION

1. Field of the Invention

The present invention relates to endoscopic image acquisition system and method and, more particularly, to a technique of collecting training images used in learning of a learning algorithm for making a diagnosis from an endoscopic image.

2. Description of the Related Art

There is known an AI (Artificial Intelligence) technique of automatically detecting or automatically discriminating a lesion in an endoscopic image using a computer to make a diagnosis. In particular, the use of a learning algorithm such as a neural network enables a highly accurate diagnosis. On the other hand, collecting training images is necessary for development of a learning algorithm.

In addition, in terms of the endoscopic diagnosis, there are observation under special light such as NBI (Narrow Band Imaging, registered trademark) and BLI (Blue Laser Imaging, registered trademark) as well as observation under white light that is commonly performed.

To collect these training images, images of a single lesion need to be captured in a plurality of light source modes. Therefore, a doctor repeats a light-source switching operation and an image capturing operation every time the doctor finds a lesion. As a result, there are problems that a load of the doctor increases and time taken for examination increases.

To cope with such problems, JP2016-202411A discloses fluorescent light observation apparatus including a reflected light imaging unit that captures an image of reflected light rays of band light rays emitted from a light source unit at a photographic subject, and a fluorescent light imaging unit that captures images of a plurality of fluorescent light rays of different bands generated by two or more of band light rays. The fluorescent light observation apparatus simultaneously captures images of the reflected light rays and the fluorescent light rays.

SUMMARY OF THE INVENTION

The fluorescent light observation apparatus of JP2016-202411A causes a display unit to display, for each frame, a fluorescence image of a different band. However, there is a problem that a frequent change in display color makes it difficult for a doctor to observe images.

The present invention is made in view of such a circumstance and it is an object of the present invention to provide endoscopic image acquisition system and method that make observation of images easier when images are collected.

To achieve the object described above, an endoscopic image acquisition system according to one aspect is an endoscopic image acquisition system including an irradiation unit that irradiates a part to be observed in a body cavity of a patient with irradiation light; an image capturing unit that receives returning light from the part to be observed and captures images of the part to be observed; a display control unit that causes the captured images to be sequentially displayed on a display unit; a wavelength pattern changing unit that changes a wavelength pattern of the irradiation light or the returning light; an accepting unit that accepts an acquisition instruction to acquire images; an image capturing control unit that causes images of an observation wavelength pattern to be captured at a certain frame rate and that causes images of a plurality of wavelength patterns different from one another to be sequentially captured in response to acceptance of the acquisition instruction; and a storage control unit that causes the images of the plurality of wavelength patterns different from one another to be stored in a storage unit, wherein the display control unit sets an image of a wavelength pattern other than the observation wavelength pattern not to be displayed.

According to this aspect, images of an observation wavelength pattern are captured at a certain frame rate. In response to acceptance of an acquisition instruction, images of a plurality of wavelength patterns different from one another are sequentially captured. At that time, the images of the plurality of wavelength patterns different from one another are stored in a storage unit, and an image of a wavelength pattern other than the observation wavelength pattern is set not to be displayed. Thus, images of a plurality of wavelength patterns different from one another can be collected, and observation of the images can be made easier.

Preferably, the display control unit displays a latest image among already captured images of the observation wavelength pattern or an image captured before the latest image by a certain number of images, instead of displaying an image of a wavelength pattern other than the observation wavelength pattern. Since only images of the observation wavelength pattern are displayed in this manner, observation of the images can be made easier.

Preferably, the endoscopic image acquisition system further includes an interpolation image creation unit that creates an interpolation image from a plurality of images including a latest image among captured images of the observation wavelength pattern or an image captured before the latest image by a certain number of images, wherein the display control unit displays the interpolation image instead of displaying an image of a wavelength pattern other than the observation wavelength pattern. Since only images of the observation wavelength pattern are displayed in this manner, observation of the images can be made easier.

Preferably, the irradiation unit includes a plurality of light sources, and the wavelength pattern changing unit selects a light source to be turned on from among the plurality of light sources to change the wavelength pattern of the irradiation light. In this manner, the wavelength pattern of the irradiation light can be appropriately changed.

Preferably, the irradiation unit includes a plurality of light sources, and the wavelength pattern changing unit changes a ratio between light quantities of the plurality of light sources to change the wavelength pattern of the irradiation light. In this manner, the wavelength pattern of the irradiation light can be appropriately changed.

Preferably, the image capturing unit includes a filter that limits a wavelength range of light transmitting through the filter, and the wavelength pattern changing unit controls the filter to change the wavelength pattern of the returning light. In this manner, the wavelength pattern of the returning light can be appropriately changed.

Preferably, the images of the plurality of wavelength patterns different from one another include an image of the observation wavelength pattern, and the storage control unit causes the image of the observation wavelength pattern to be stored in a first storage area of the storage unit, and causes an image of a wavelength pattern other than the observation wavelength pattern to be stored in a second storage area of the storage unit, the second storage area being different from the first storage area. In this manner, a diagnosis image and a training image can be stored in different areas of a storage unit. Note that storing a diagnosis image and a training image in different areas of a storage unit also encompasses the case where a plurality of storage units are included and a diagnosis image and a training image are stored in different storage units.

Preferably, the storage control unit causes the image to be stored in the storage unit in association with information on the wavelength pattern used in capturing of the image. In this manner, a training image associated with information on a wavelength pattern can be collected.

Preferably, the endoscopic image acquisition system further includes a wavelength pattern selection unit that allows a user to select the observation wavelength pattern, wherein the image capturing control unit causes images to be captured with the selected wavelength pattern at a certain frame rate. In this manner, images can be observed with a desired wavelength pattern.

Preferably, the endoscopic image acquisition system further includes an order selection unit that allows a user to select an order of the plurality of wavelength patterns used in sequential capturing of the images of the plurality of wavelength patterns different from one another, wherein the image capturing control unit causes the images of the plurality of wavelength patterns different from one another to be sequentially captured in the selected order. In this manner, images can be captured sequentially from a desired image.

Preferably, the endoscopic image acquisition system further includes a to-be-stored image selection unit that allows a user to select an image to be stored in the storage unit from among the images of the plurality of wavelength patterns different from one another, wherein the storage control unit causes the selected image to be stored in the storage unit. In this manner, only necessary images can be stored in the storage unit.

Preferably, the endoscopic image acquisition system further includes an automatic selection unit that automatically selects an image to be stored in the storage unit from among the images of the plurality of wavelength patterns different from one another, wherein the storage control unit causes the automatically selected image to be stored in the storage unit. In this manner, only desired images can be stored in the storage unit.

Preferably, the endoscopic image acquisition system further includes a determining unit that determines an image captured at the time of transition of the wavelength pattern when the images of the plurality of wavelength patterns different from one another are sequentially captured, wherein the automatic selection unit automatically selects the image based on a result of the determination. In this manner, an image captured at the time of transition of the wavelength pattern can be excluded from training images.

Preferably, the endoscopic image acquisition system further includes an acquisition instruction input unit with which a user inputs the acquisition instruction, wherein the accepting unit accepts the acquisition instruction from the acquisition instruction input unit. In this manner, a desired image can be acquired.

Preferably, the endoscopic image acquisition system further includes a recognition unit that recognizes a scene of interest from among the captured images; and an acquisition instruction output unit that outputs the acquisition instruction in response to the recognition unit recognizing the scene of interest, wherein the accepting unit accepts the acquisition instruction from the acquisition instruction output unit. In this manner, an image of a scene of interest can be automatically acquired.

To achieve the object described above, an endoscopic image acquisition method according to an aspect is an endoscopic image acquisition method including an irradiation step of irradiating a part to be observed in a body cavity of a patient with irradiation light; an image capturing step of receiving returning light from the part to be observed and capturing images of the part to be observed; a display control step of causing the captured images to be sequentially displayed on a display unit; a wavelength pattern changing step of changing a wavelength pattern of the irradiation light or the returning light; an accepting step of accepting an acquisition instruction to acquire images; an image capturing control step of causing images of an observation wavelength pattern to be captured at a certain frame rate and causing images of a plurality of wavelength patterns different from one another to be sequentially captured in response to acceptance of the acquisition instruction; and a storage control step of causing the images of the plurality of wavelength patterns different from one another to be stored in a storage unit, wherein the display control step sets an image of a wavelength pattern other than the observation wavelength pattern not to be displayed.

According to this aspect, images of an observation wavelength pattern are captured at a certain frame rate. In response to acceptance of an acquisition instruction, images of a plurality of wavelength patterns different from one another are sequentially captured. At that time, the images of the plurality of wavelength patterns different from one another are stored in a storage unit, and an image of a wavelength pattern other than the observation wavelength pattern is set not to be displayed. Thus, images of a plurality of wavelength patterns different from one another can be collected, and observation of the images can be made easier.

According to the present invention, observation of images can be made easier when images are collected.

BRIEF DESCRIPTION OF THE DRAWINGS

FIG. 14 is a block diagram illustrating functions of an endoscope system; and

FIG. 15 is a block diagram illustrating functions of an endoscope system.

DESCRIPTION OF THE PREFERRED EMBODIMENTS

Preferred embodiments of the present invention will be described in detail below in accordance with the accompanying drawings.

First Embodiment

Figure 1:
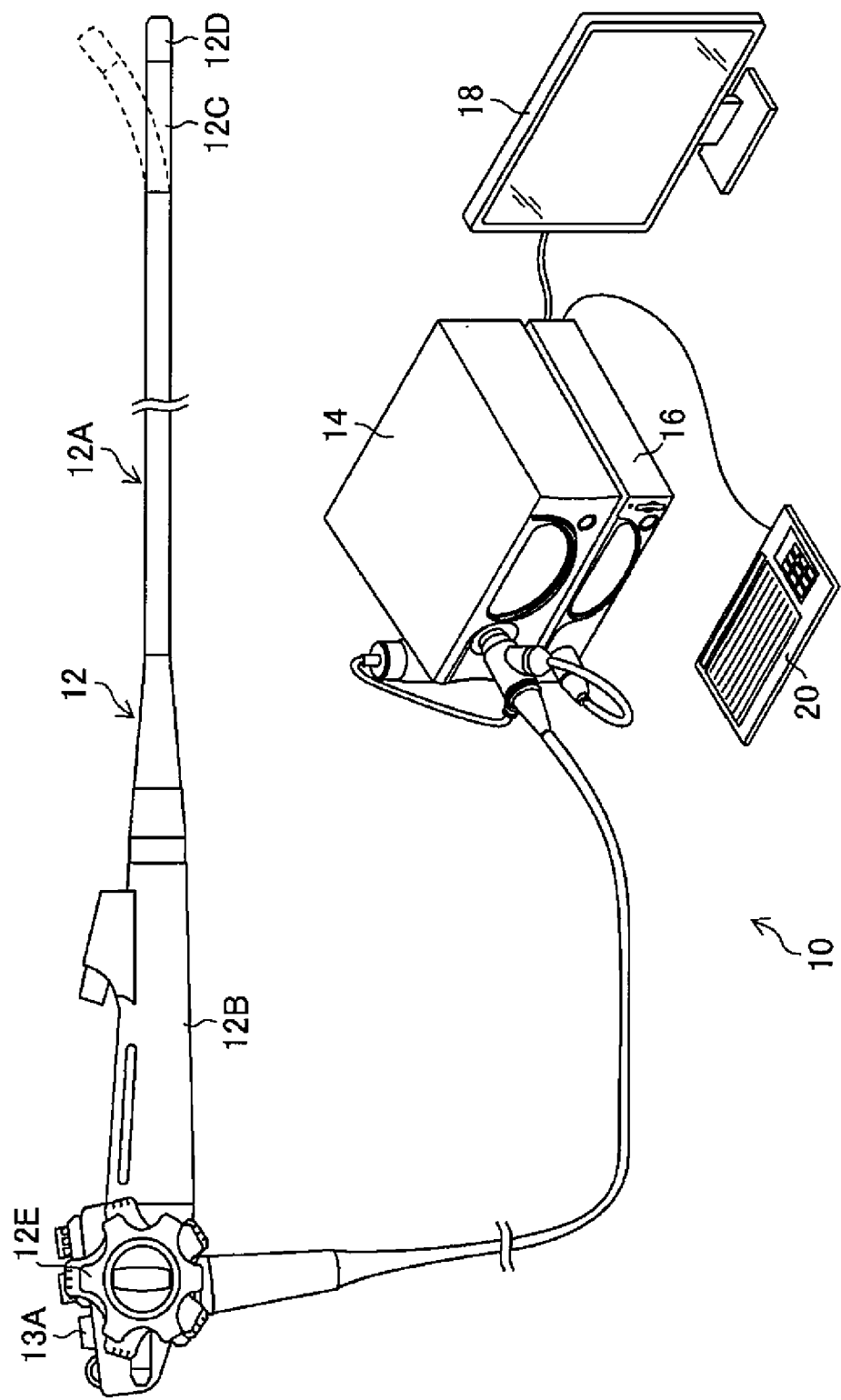
FIG. 1 is an external view of an endoscope system.

FIG. 1 is an external view of an endoscope system 10 (an example of an endoscopic image acquisition system) according to a first embodiment. As illustrated in FIG. 1, the endoscope system 10 includes an endoscope 12, a light source device 14, a processor device 16, a display unit 18, and an input unit 20.

The endoscope 12 is optically connected to the light source device 14. The endoscope 12 is also electrically connected to the processor device 16.

The endoscope 12 has an insertion part 12A to be inserted into a body cavity of a patient, an operation unit 12B provided at a proximal end portion of the insertion part 12A, and a bending part 12C and a tip part 12D that are provided on the distal end side of the insertion part 12A.

The operation unit 12B is provided with an angle knob 12E and a mode switch 13A. The operation unit 12B is also provided with an acquisition instruction input unit 13B (see FIG. 2).

An operation on the angle knob 12E causes a bending action of the bending part 12C. Through this bending action, the tip part 12D is directed toward a desired direction.

The mode switch 13A is used for an observation mode switching operation. The endoscope system 10 has a plurality of observation modes for which wavelength patterns of irradiation light are different from one another. A doctor can set a desired observation mode by operating the mode switch 13A. The endoscope system 10 generates an image according to the set observation mode using a combination of the wavelength pattern and image processing and displays the image on the display unit 18.

The endoscope system 10 is capable of acquiring a still image of a desired position. In the present embodiment, the endoscope system 10 is capable of acquiring a diagnosis image for used in creation of a diagnosis report and a training image for use in learning of a learning algorithm. The acquisition instruction input unit 13B (an example of an accepting unit) is an interface used by a doctor to input a still image acquisition instruction. The acquisition instruction input unit 13B accepts the still image acquisition instruction. The still image acquisition instruction accepted by the acquisition instruction input unit 13B is input to the processor device 16.

The processor device 16 is electrically connected to the display unit 18 and the input unit 20. The display unit 18 is a display device that outputs or displays an image to be observed, information relating to the image to be observed, and so on. The input unit 20 functions as a user interface that accepts input operations of function settings, various instructions, and so on of the endoscope system 10.

Figure 2:
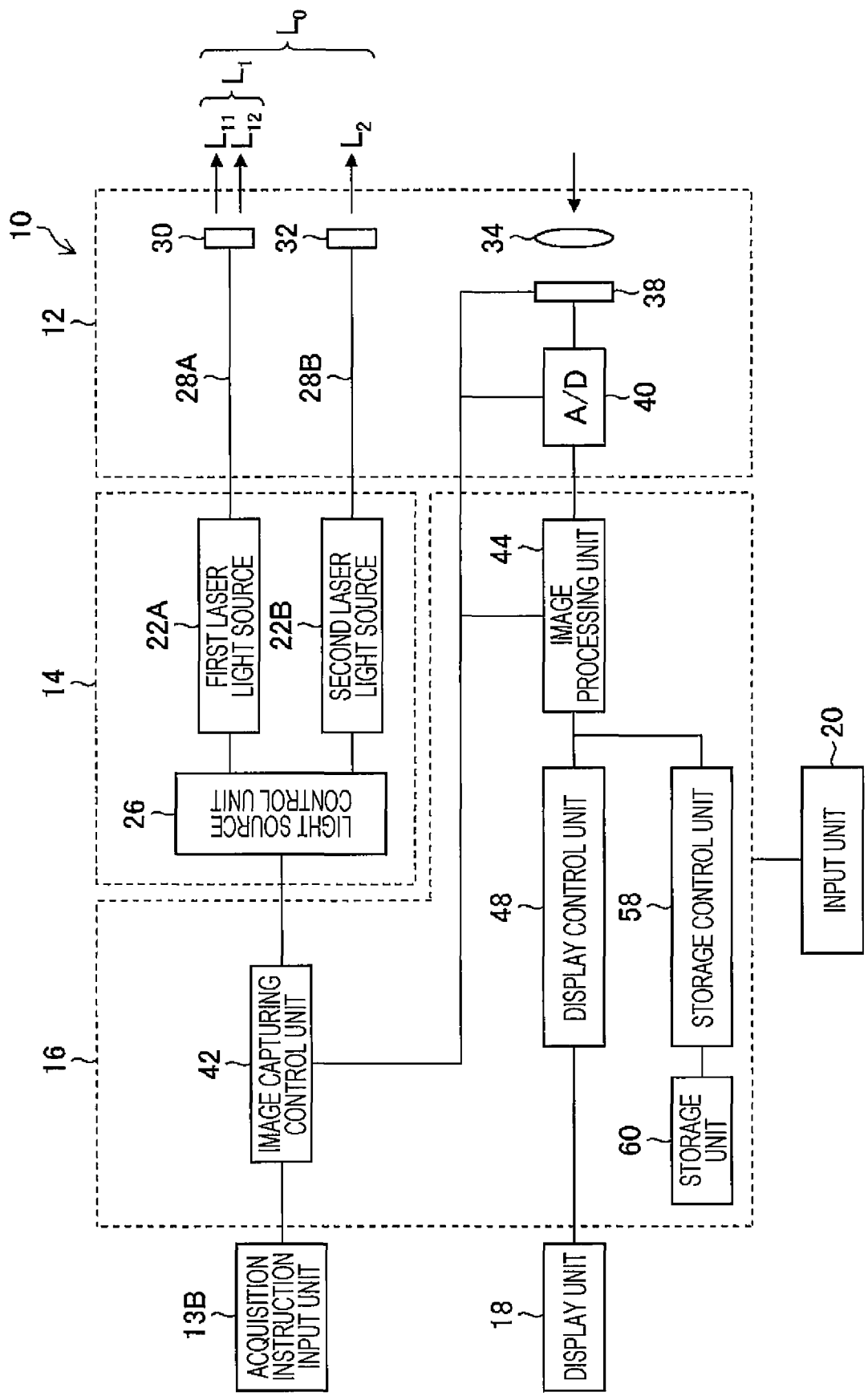
FIG. 2 is a block diagram illustrating functions of the endoscope system.

FIG. 2 is a block diagram illustrating functions of the endoscope system 10. As illustrated in FIG. 2, the light source device 14 includes a first laser light source 22A, a second laser light source 22B, and a light source control unit 26.

The first laser light source 22A is a blue laser light source having a center wavelength of 445 nm. The second laser light source 22B is a violet laser light source having a center wavelength of 405 nm. Laser diodes can be used as the first laser light source 22A and the second laser light source 22B. Light emission of the first laser light source 22A and light emission of the second laser light source 22B are separately controlled by the light source control unit 26. A ratio between intensity of light emitted by the first laser light source 22A and intensity of light emitted by the second laser light source 22B is changeable in any manner.

In addition, as illustrated in FIG. 2, the endoscope 12 includes an optical fiber 28A, an optical fiber 28B, a fluorescent body 30, a diffusion member 32, an imaging lens 34, an imaging element 38, and an analog-to-digital converter 40.

The first laser light source 22A, the second laser light source 22B, the optical fiber 28A, the optical fiber 28B, the fluorescent body 30, and the diffusion member 32 constitute an irradiation unit.

The fluorescent body 30 disposed at the tip part 12D of the endoscope 12 is irradiated with laser light emitted from the first laser light source 22A through the optical fiber 28A. The fluorescent body 30 includes a plurality of kinds of fluorescent bodies that absorb part of blue laser light emitted from the first laser light source 22A to be excited and emit green to yellow light. Accordingly, green to yellow excitation light $L_{11}$ for which blue laser light emitted from the first laser light source 22A has served as excitation light and blue laser light $L_{12}$ that has transmitted through the fluorescent body 30 without being absorbed are combined. Consequently, the light outgoing from the fluorescent body 30 is white (pseudo-white) light $L_1$.

Note that white light used herein is not limited light strictly including all the wavelength components of visible light. For example, white light may be light including light of particular wavelength ranges such as light of R (red), G (green), and B (blue). It is assumed that white light includes in a broad sense light including wavelength components of green to red, light including wavelength components of blue to green, and so on.

On the other hand, the diffusion member 32 disposed at the tip part 12D of the endoscope 12 is irradiated with laser light emitted from the second laser light source 22B through the optical fiber 28B. A resin material having a light-transmitting property or the like can be used as the diffusion member 32. Light outgoing from the diffusion member 32 is light $L_2$ of a narrow wavelength range having a homogeneous quantity of light in an irradiation region.

Figure 3:
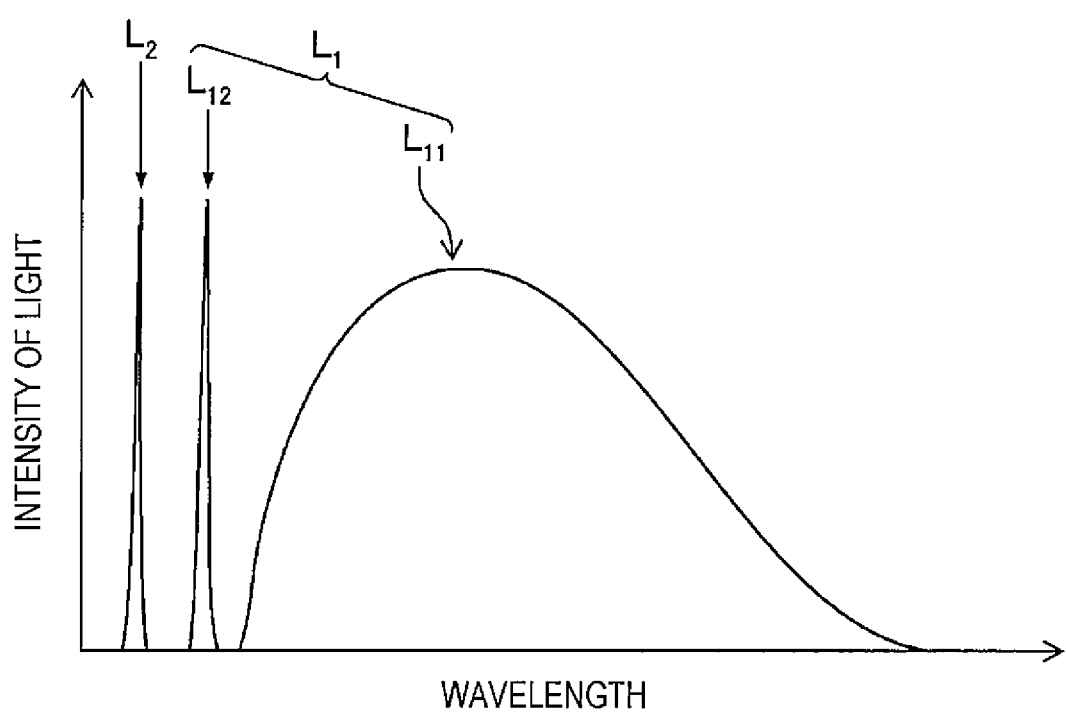
FIG. 3 is a graph illustrating a light intensity distribution.

FIG. 3 is a graph illustrating a light intensity distribution of the light $L_1$ and the light $L_2$. The light source control unit 26 (an example of a wavelength pattern changing unit) changes a light-quantity ratio between the first laser light source 22A and the second laser light source 22B. In this manner, the light-quantity ratio between the light $L_1$ and the light $L_2$ is changed, so that a wavelength pattern of irradiation light $L_0$ which is the combined light of the light $L_1$ and the light $L_2$ is changed. Thus, a part to be observed can be irradiated with the irradiation light $L_0$ having characteristics that are different from one another.

As described above, the endoscope system 10 has a plurality of observation modes. It is assumed herein that the endoscope system 10 has three observation modes, that is, a mode MA, a mode MB, and a mode MC. Note that the number of observation modes is not limited to three.

The light-quantity ratio between light emitted from the first laser light source 22A and light emitted from the second laser light source 22B in the mode MA is 1:0. A wavelength pattern of the irradiation light $L_0$ generated based on this light-quantity ratio is referred to as a wavelength pattern PA. In the mode MA, a white light image can be acquired.

The light-quantity ratio between light emitted from the first laser light source 22A and light emitted from the second laser light source 22B in the mode MB is 1:4. A wavelength pattern of the irradiation light $L_0$ generated based on this light-quantity ratio is referred to as a wavelength pattern PB. In the mode MB, an image in which blood vessels and structures of a skin layer of a biological tissue are emphasized can be acquired.

The light-quantity ratio between light emitted from the first laser light source 22A and light emitted from the second laser light source 22B in the mode MC is 7:1. A wavelength pattern of the irradiation light L generated based on this light-quantity ratio is referred to as a wavelength pattern PC. In the mode MC, an image in which blood vessels and surface structures in an intermediate to distant range are emphasized can be acquired.

Note that the quantity of the irradiation light $L_0$ in each of the wavelength patterns PA, PB, and PC is appropriately adjusted.

The description now returns to FIG. 2. The imaging lens 34, the imaging element 38, and the analog-to-digital converter 40 constitute an image capturing unit. The image capturing unit is disposed in the tip part 12D of the endoscope 12.

Returning light including reflected light of the irradiation light $L_0$ from a part to be observed and/or self-fluorescence from the part to be observed is incident to the imaging lens 34. The imaging lens 34 forms an image of the incident light onto the imaging element 38. The imaging element 38 generates an analog signal based on the received light. A CCD (Charge Coupled Device) image sensor or a CMOS (Complementary Metal Oxide Semiconductor) image sensor is used as the imaging element 38. The analog signal output from the imaging element 38 is converted into a digital signal by the analog-to-digital converter 40, and the digital signal is input to the processor device 16.

In addition, as illustrated in FIG. 2, the processor device 16 includes an image capturing control unit 42, an image processing unit 44, a display control unit 48, a storage control unit 58, and a storage unit 60.

The still image acquisition instruction accepted by the acquisition instruction input unit 13B is input to the image capturing control unit 42. The image capturing control unit 42 controls the light source control unit 26 of the light source device 14, the imaging element 38 and the analog-to-digital converter 40 of the endoscope 12, and the image processing unit 44 of the processor device 16. The image capturing control unit 42 centrally controls capturing of moving images and still images performed by the endoscope system 10.

The image processing unit 44 performs image processing on the digital signal input from the analog-to-digital converter 40 of the endoscope 12 to generate image data (hereinafter, referred to as an image) representing an image.

The image processing unit 44 performs image processing according to a wavelength pattern of irradiation light $L_0$ used at the time of image capturing.

The display control unit 48 causes the display unit 18 to sequentially display images generated by the image processing unit 44.

In addition, the storage control unit 58 causes the storage unit 60 to store an image captured in accordance with a still image acquisition instruction, information relating to the image, and so on. The storage unit 60 is, for example, a storage device such as a hard disk. Note that the storage unit 60 is not limited to a storage device built in the processor device 16. For example, the storage unit 60 may be an external storage device (not illustrated) that is connected to the processor device 16. The external storage device may be connected via a network.

The endoscope system 10 thus configured usually captures a moving image at a certain frame rate and displays the captured moving image on the display unit 18. In addition, when a still image acquisition instruction is input from the acquisition instruction input unit 13B, the endoscope system 10 captures a still image and stores the still image in the storage unit 60.

A training image collection method according to the first embodiment performed by the endoscope system 10 will be described. Here, still images are acquired which are captured by radiating the irradiation light $L_0$ of each of the three wavelength patterns PA, PB, and PC in response to a still image acquisition instruction. In addition, an image of a wavelength pattern that is the same as the wavelength pattern of the irradiation light $L_0$ of the observation mode is stored as a diagnosis image. An image of a wavelength pattern that is different from the wavelength pattern of the irradiation light $L_0$ of the observation mode is stored as a training image.

Figure 4:
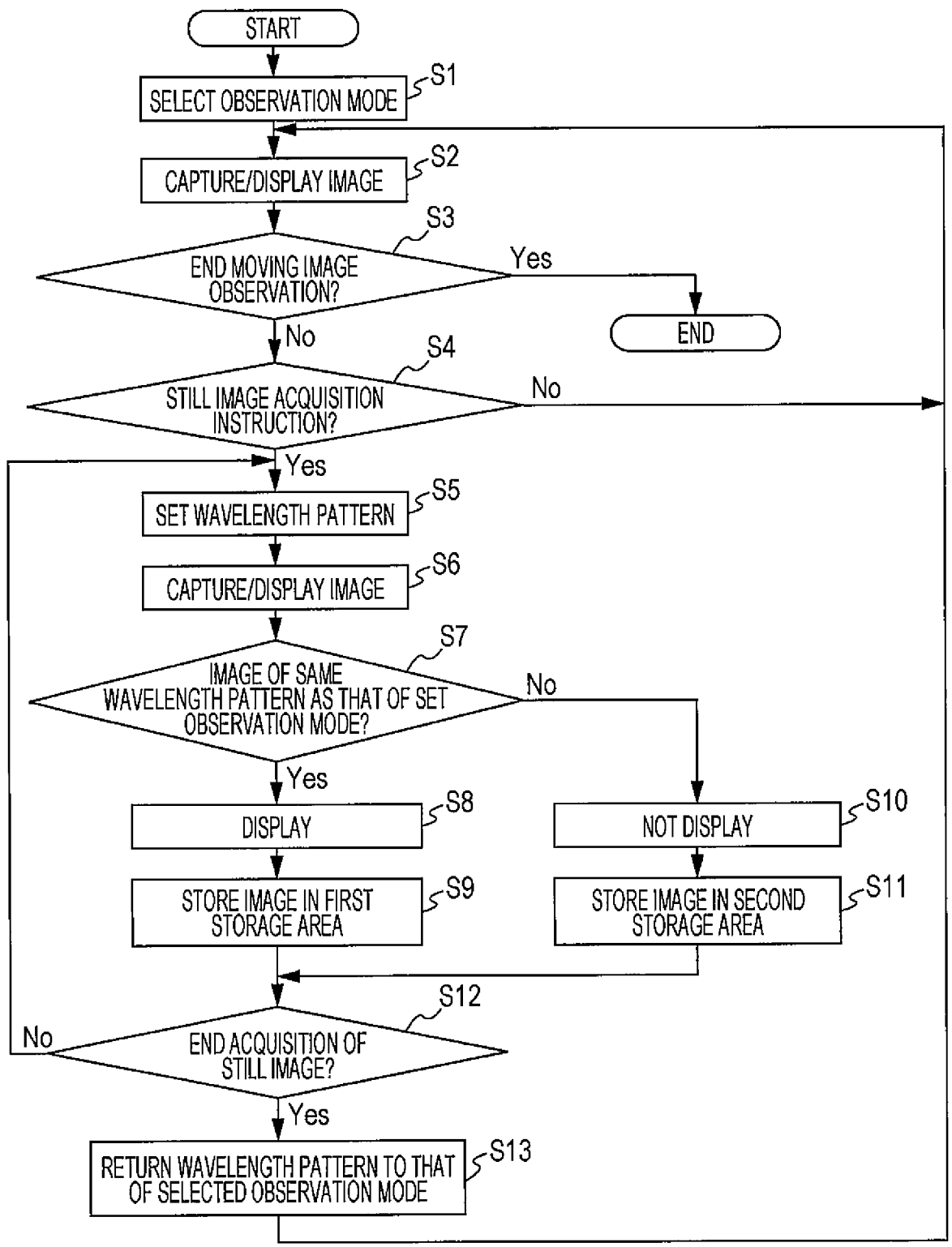
FIG. 4 is a flowchart illustrating a process of a training image collection method.
Figure 5:
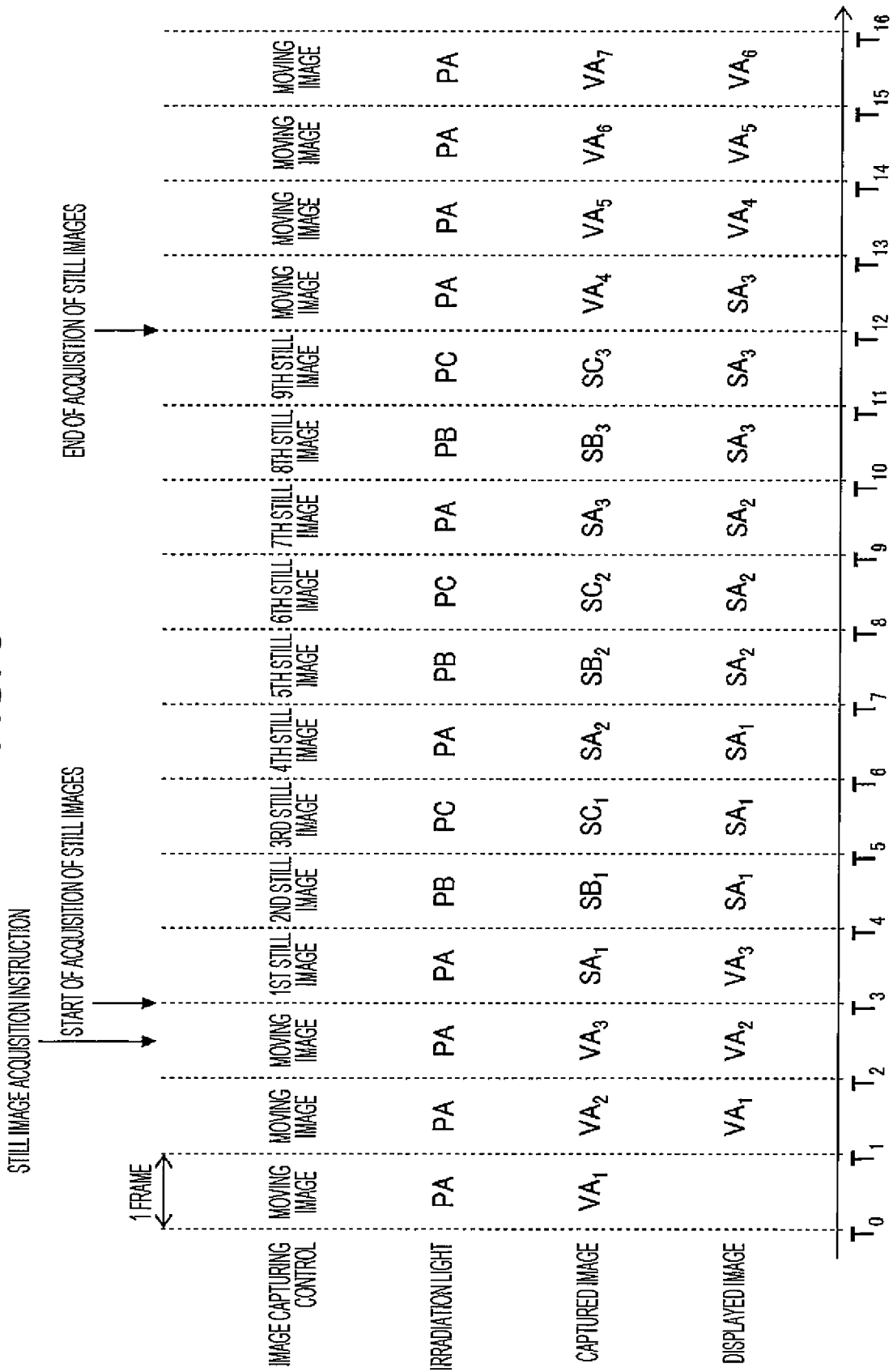
FIG. 5 is a timing chart describing the process of the training image collection method.

FIG. 4 is a flowchart illustrating a process of the training image collection method (an example of an endoscopic image acquisition method) in moving image observation. In addition, FIG. 5 is a timing chart describing the process of the training image collection method. In FIG. 5, a period from time $T_N$ to time $T_{N+1}$ (where N=0 to 15) indicates a frame rate of image capturing and each is 1/30 seconds.

To start moving image observation, a doctor selects an observation mode for capturing a moving image (an observation wavelength pattern) from among the modes MA, MB, and MC by using the input unit 20 (an example of a wavelength pattern selection unit) in step S1. Here, the doctor selects the mode MA, for example. Note that the observation mode for capturing a moving image can be appropriately changed even during capturing of a moving image. In addition, the observation mode for capturing a moving image may be determined in advance.

Then, the doctor inserts the insertion part 12A of the endoscope 12 into a body cavity of a patient. The observation mode for capturing a moving image may be selected after the insertion of the endoscope 12.

Subsequently, in step S2, a moving image is captured in the observation mode selected in step S1 and the resulting moving image is displayed. Specifically, the light source control unit 26 sets the light emitted from the first laser light source 22A and the light emitted from the second laser light source 22B to have a light-quantity ratio corresponding to the observation mode selected in step S1. Consequently, a part to be observed in the body cavity of the patient is irradiated with the irradiation light $L_0$ of the desired wavelength pattern (an example of an irradiation step, and an example of a wavelength pattern changing step).

In addition, the image capturing control unit 42 controls the imaging element 38, the analog-to-digital converter 40, and the image processing unit 44 to acquire an image of the part to be observed based on received light returning from the part to be observed (an example of an image capturing step). Further, the display control unit 48 causes the display unit 18 to display the image generated by the image processing unit 44 (an example of a display control step).

In an example illustrated in FIG. 5, an image $VA_1$ is captured in a period from time $T_0$ to time $T_1$. In addition, the image $VA_1$ is displayed and a following image $VA_2$ is captured in a subsequent period from time $T_1$ to time $T_2$. Further, the image $VA_2$ is displayed and a following image $VA_3$ is captured in a subsequent period from time $T_2$ to time $T_3$.

In this manner, images are captured at a certain frame rate. In addition, the captured images are displayed on the display unit 18 at a timing that is delayed by one frame.

Processing of steps S3 to S13 described below is performed as an interrupt process of moving-image capturing performed in step S2.

In step S3, it is determined whether or not an instruction to end the moving image observation is input. The doctor can input the instruction to end the moving image observation by using the input unit 20. If the instruction to end is input, the process illustrated in this flowchart ends.

If the instruction to end moving image observation is not input, the process proceeds to step S4. In step S4, the image capturing control unit 42 determines whether or not a still image acquisition instruction is input. As described before, the doctor can input the still image acquisition instruction from the acquisition instruction input unit 13B. If the acquisition instruction is not input, the process returns to step S2, and the similar processing is repeated. That is, capturing of the moving image is continued. If it is determined that the still image acquisition instruction is input (an example of an accepting step), the process proceeds to step S5.

In step S5 and subsequent steps, acquisition of still images is performed. Herein, description will be given of a case where nine still images in total are acquired by repeatedly performing three times a process of capturing of one still image with the wavelength pattern PA, capturing of one still image with the wavelength pattern PB, and capturing one still image with the wavelength pattern PC.

In the example illustrated in FIG. 5, a still image acquisition instruction is input in the period from time $T_2$ to time $T_3$. In this period from time $T_2$ to time $T_3$, the image $VA_3$ is captured under the control of the image capturing control unit 42. Thus, a still image acquisition process is started from time $T_3$ which is the next image capturing start timing.

First in step S5, the light source control unit 26 sets the wavelength pattern. Here, the first still image is a still image of the wavelength pattern PA. Therefore, the light source control unit 26 sets the light emitted from the first laser light source 22A and the light emitted from the second laser light source 22B to have a light-quantity ratio of the wavelength pattern PA. Consequently, a part to be observed is irradiated with the irradiation light $L_0$ of the wavelength pattern PA.

Next in step S6, capturing of still images is performed. Specifically, the image capturing control unit 42 controls the imaging element 38, the analog-to-digital converter 40, and the image processing unit 44 to capture an image $SA_1$ of the part to be observed (an example of an image capturing step). In addition, the display control unit 48 displays on the display unit 18 the image $VA_3$ which is the latest captured image at this time point.

Subsequently in step S7, the display control unit 48 determines whether or not the image $SA_1$ captured in step S6 is an image of the same wavelength pattern as the wavelength pattern of the observation mode selected in step S1, that is, whether or not the wavelength pattern of the irradiation light $L_0$ for the image $SA_1$ is the same as the wavelength pattern of the irradiation light $L_0$ of the observation mode selected in step S1. Here, the image $SA_1$ is an image of the wavelength pattern PA. In addition, the observation mode selected in step S1 is the mode MA, and the wavelength pattern in the mode MA is the wavelength pattern PA. Since the wavelength patterns are the same in this manner, YES is determined and the process proceeds to step S8.

In step S8, the display control unit 48 sets the image $SA_1$ captured in step S6 as a to-be-displayed image. In addition, in subsequent step S9, the storage control unit 58 stores the image $SA_1$ in a first storage area of the storage unit 60 in association with information on the wavelength pattern PA of the irradiation light $L_0$ used in capturing of the image $SA_1$ (an example of a storage control step). The first storage area is an area for storing a diagnosis image. The first storage area is, for example, one drive among a plurality of drives of the storage unit 60 or one folder among a plurality of folders.

Next in step S12, it is determined whether or not acquisition of still images is finished. Here, since acquisition of still images is not finished, the process returns to step S5.

Here, a second still image (a first still image in the mode MB) is captured from time $T_4$. Specifically, in step S5, the light emitted from the first laser light source 22A and the light emitted from the second laser light source 22B are set to have a light-quantity ratio of the wavelength pattern PB. Then in step S6, an image $SB_1$ is captured. In addition, since the image $SA_1$ is set as a to-be-displayed image in previous step S8, the display control unit 48 causes the display unit 18 to display the image $SA_1$ from time $T_4$.

Subsequently in step S7, the display control unit 48 determines whether or not the image $SB_1$ captured in step S6 is an image of the same wavelength pattern as the wavelength pattern of the observation mode selected in step S1, that is, whether or not the wavelength pattern of the irradiation light $L_0$ for the image $SB_1$ is the same as the wavelength pattern of the irradiation light $L_0$ of the observation mode selected in step S1. Here, the image $SB_1$ is an image of the wavelength pattern PB. In addition, the observation mode selected in step S1 is the mode MA, and the wavelength pattern in the mode MA is the wavelength pattern PA. Since the wavelength patterns are different in this manner, NO is determined and the process proceeds to step S10.

In step S10, the display control unit 48 sets the image $SB_1$ captured in step S6 not to be displayed. In addition, in subsequent step S11, the storage control unit 58 stores the image $SB_1$ in a second storage area of the storage unit 60 in association with information on the wavelength pattern PB of the irradiation light $L_0$ used in capturing of the image $SB_1$ (an example of the storage control step). The second storage area is an area for storing training images. The second storage area is, for example, one drive among a plurality of drives of the storage unit 60 or one folder among a plurality of folders and is an area different from the first storage area. The storage unit 60 may be used as the first storage area, and a storage device different from the storage unit 60 may be used as the second storage area.

Next in step S12, it is determined whether or not acquisition of still images is finished. Here, since acquisition of still images is not finished, the process returns to step S5.

Here, a third still image (a first still image in the mode MC) is captured from time $T_5$. Specifically, in step S5, the light emitted from the first laser light source 22A and the light emitted from the second laser light source 22B are set to have a light-quantity ratio of the wavelength pattern PC. Then in step S6, an image $SC_1$ is captured.

Note that since the image $SB_1$ is set not to be displayed in previous step S10, the display control unit 48 does not display the image $SB_1$ on the display unit 18. Here, instead of the image $SB_1$, the image $SA_1$ that is displayed from time $T_4$ is continuously displayed on the display unit 18.

Subsequently in step S7, the display control unit 48 determines whether or not the image $SC_1$ captured in step S6 is an image of the same wavelength pattern as the wavelength pattern of the observation mode selected in step S1, that is, whether or not the wavelength pattern of the irradiation light $L_0$ for the image SCI is the same as the wavelength pattern of the irradiation light $L_0$ of the observation mode selected in step S1. Here, the image $SC_1$ is an image of the wavelength pattern PC. In addition, the observation mode selected in step S1 is the mode MA, and the wavelength pattern in the mode MA is the wavelength pattern PA. Since the wavelength patterns are different in this manner, NO is determined and the process proceeds to step S10.

In step S10, the display control unit 48 sets the image $SC_1$ not to be displayed. In addition, in subsequent step S11, the storage control unit 58 stores the image $SC_1$ in the second storage area of the storage unit 60 in association with information on the wavelength pattern PC of the irradiation light $L_0$ used in capturing of the image $SC_1$.

Next in step S12, it is determined whether or not acquisition of still images is finished. Here, since acquisition of still images is not finished yet, the process returns to step S5.

Likewise, an image $SA_2$ which is a fourth still image (a second still image in the mode MA) is captured with the irradiation light $L_0$ of the wavelength pattern PA from time $T_6$ (steps S5 and S6). In addition, since the image SC is set not to be displayed in previous step S10, the display control unit 48 does not display the image $SC_1$ on the display unit 18. Here, instead of the image $SC_1$, the image $SA_1$ that is displayed from time $T_4$ is continuously displayed on the display unit 18.

Here, the image $SA_2$ is an image of the same wavelength pattern as the wavelength pattern of the observation mode selected in step S1. Thus, YES is determined in step S7, and the process proceeds to step S8.

In step S8, the image $SA_2$ is set as a to-be-displayed image. In addition, in step S9, the image $SA_2$ is stored in the first storage area of the storage unit 60 in association with information on the wavelength pattern PA of the irradiation light $L_0$ used in capturing of the image $SA_2$.

Next in step S12, it is determined whether or not acquisition of still images is finished. Here, since acquisition of still images is not finished yet, the process returns to step S5.

Likewise, an image $SB_2$ which is a fifth still image (a second still image in the mode MB) is captured with the irradiation light $L_0$ of the wavelength pattern PB from time $T_7$ (steps S5 and S6). In addition, since the image $SA_2$ is set as a to-be-displayed image in previous step S8, the display control unit 48 causes the display unit 18 to display the image $SA_2$.

Here, the image $SB_2$ is not an image of the same wavelength pattern as the wavelength pattern of the observation mode selected in step S1. Thus, NO is determined in step S7, and the process proceeds to step S10.

In step S10, the display control unit 48 sets the image $SB_2$ not to be displayed. In addition, in subsequent step S11, the storage control unit 58 stores the image $SB_2$ in the second storage area of the storage unit 60 in association with information on the wavelength pattern PB of the irradiation light $L_0$ used in capturing of the image $SB_2$.

Next in step S12, it is determined whether or not acquisition of still images is finished. Here, since acquisition of still images is not finished yet, the process returns to step S5.

Thereafter, sixth to ninth still images, that is, an image $SC_2$ which is a second still image captured with the wavelength pattern PC, an image $SA_3$ which is a third still image captured with the wavelength pattern PA, an image $SB_3$ which is a third still image captured with the wavelength pattern PB, and an image $SC_3$ which is a third still image captured with the wavelength pattern PC, are sequentially captured.

After capturing of all the still images is finished, it is determined in step S12 that acquisition of still images is finished. The process proceeds to step S13.

In step S13, the wavelength pattern of the irradiation light $L_0$ is returned to the wavelength pattern of the observation mode selected in step S1. Here, the wavelength pattern of the irradiation light $L_0$ is returned to the wavelength pattern PA. The process then returns to step S2, and the similar processing is repeated.

Note that the image $SC_3$ captured lastly is set not to be displayed in step S10. Thus, when capturing of a moving image is restarted after the process returns to step S2, the image $SC_3$ is not displayed on the display unit 18. Here, instead of the image $SC_3$, the image $SA_3$ that is displayed from time $T_{10}$ is continuously displayed on the display unit 18.

Note that an image captured in the previous frame is displayed on the display unit 18 from time $T_{13}$.

By performing collection of training images in the above-described manner, training still images are successfully captured and stored. In addition, at a display timing of a still image of the wavelength pattern that is different from the wavelength pattern of the irradiation light $L_0$ of the selected observation mode (an example of a display timing of an image of a wavelength pattern other than an observation wavelength pattern), the latest image among images of the same wavelength patterns as the wavelength pattern of the irradiation light $L_0$ of the selected observation mode (an example of a latest image among already captured images of the observation wavelength pattern) is displayed. This makes the display color during acquisition of still images be the same color as the display color during acquisition of a moving image, making observation using the display unit 18 easier.

Second Embodiment

The order in which still images are acquired and the number of still images to be acquired are not limited to the examples described in the first embodiment.

For example, a doctor may designate the number of still images to be acquired by using the input unit 20. In the first embodiment, three still images are acquired with each of the wavelength patterns. Alternatively, two or four or more still images may be acquired with each of the wavelength patterns. As described above, as many still images as required can be captured.

In addition, the doctor may select the acquisition order by using the input unit 20 (an example of an order selection unit). In the first embodiment, still images are acquired in an order of the wavelength pattern PA, the wavelength pattern PB, and the wavelength pattern PC. Alternatively, still images can be acquired in a desired order, for example, in an order of the wavelength pattern PB, the wavelength pattern PC, and the wavelength pattern PA, in an order of the wavelength pattern PC, the wavelength pattern PA, and the wavelength pattern PB, or in an order of the wavelength pattern PC, the wavelength pattern PB, and the wavelength pattern PA.

In addition, a plurality of images of the same wavelength pattern may be acquired continuously. For example, in an example of a timing chart illustrated in FIG. 6, nine still images in total are acquired by continuously capturing three still images with the wavelength pattern PA, continuously capturing three still images with the wavelength pattern PB, and continuously capturing three still images with the wavelength pattern PC. Note that in this example the latest image $SA_3$ captured with the wavelength pattern PA is displayed in a period from time $T_6$ to time $T_{13}$.

Further, a continuous image capturing process may be repeatedly performed a plurality of times. For example, the order may be set such that 18 still images in total are acquired by performing twice a process of continuously capturing three still images with the wavelength pattern PA, continuously capturing three still images with the wavelength pattern PB, and continuously capturing three still images with the wavelength pattern PC.

It is anticipated that adhesion of dust onto the imaging lens 34, a difficulty in maintaining an imaging angle, and the like make it difficult to acquire a desired image in capturing of endoscopic images if elapsed time from input of an image capturing instruction increases. Thus, it is preferable to allow for designation of an order of wavelength patterns used for image capturing in order to capture an image of a waveform pattern considered to be important first.

In addition, a doctor may select a wavelength pattern with which still images are to be acquired, by using the input unit 20. For example, if still images of the wavelength pattern PB are not necessary, only still images of the wavelength pattern PA and still images of the wavelength pattern PC can be captured.

Third Embodiment

At a display timing of a still image of a wavelength pattern that is different from the wavelength pattern of the irradiation light $L_0$ of the selected observation mode, an image captured before the latest image by a certain number of images may be displayed.

Figure 7:
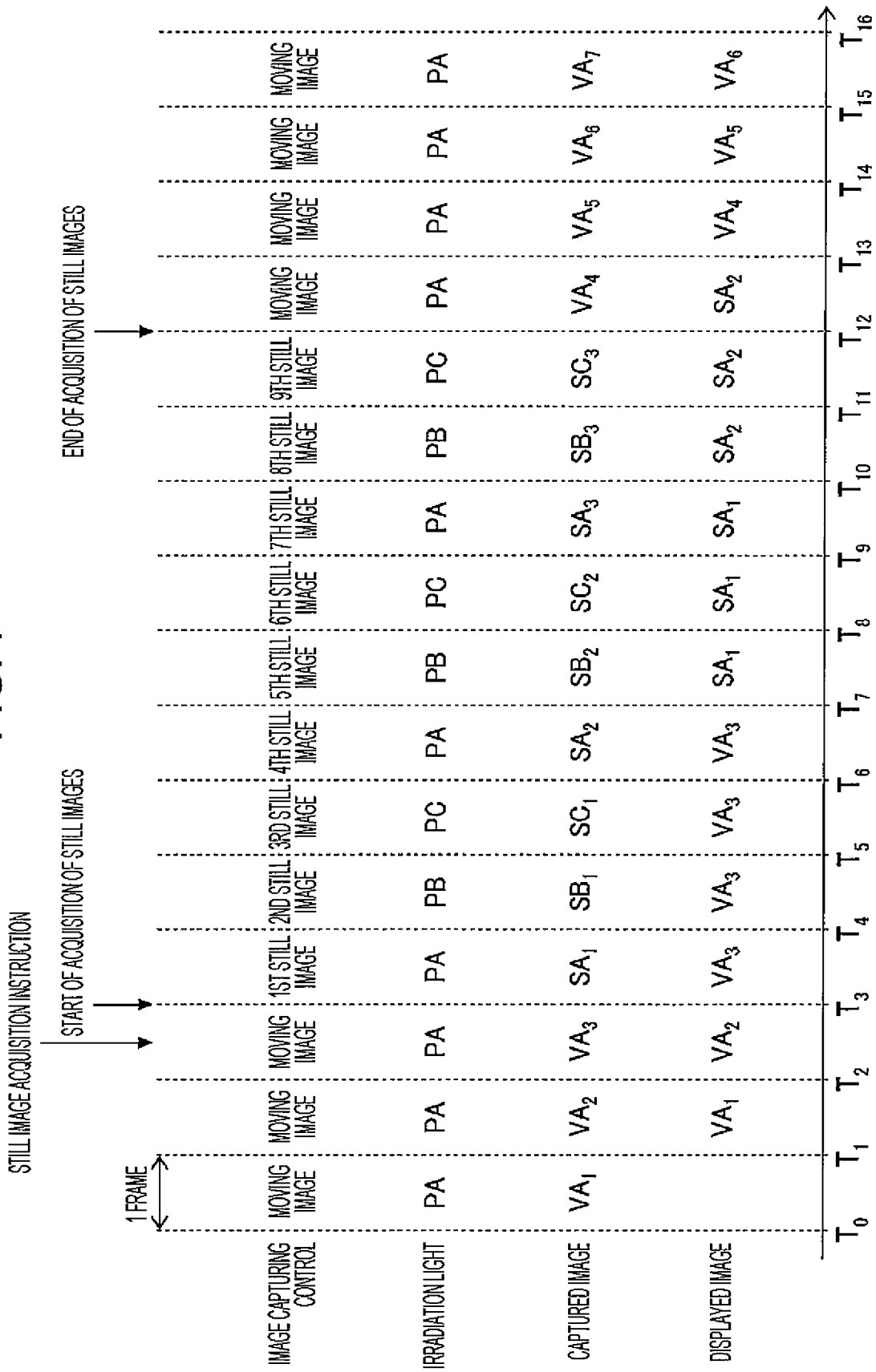
FIG. 7 is a timing chart describing the process of the training image collection method.

FIG. 7 is a timing chart describing a process of a training image collection method according to the third embodiment performed by the endoscope system 10.

Here, instead of an image $SA_1$ which is the latest image captured with the irradiation light $L_0$ of the waveform pattern PA, an image $VA_3$ which is an image captured with the irradiation light $L_0$ of the wavelength pattern PA before the latest image $SA_1$ by one image is displayed in a period from time $T_4$ to time $T_7$.

In addition, instead of an image $SA_2$ which is the latest image captured with the irradiation light $L_0$ of the wavelength pattern PA, the image $SA_1$ which is an image captured with the irradiation light $L_0$ of the wavelength pattern PA before the latest image $SA_2$ by one image is displayed in a period from time $T_7$ to time $T_{10}$.

Likewise, an image $SA_2$ which is an image captured before the latest image $SA_3$ by one image is displayed in a period from time $T_{10}$ to time $T_{13}$.

Here, an image captured before the latest image by one image is displayed. Alternatively, an image captured further before may be displayed. As described above, even when an image captured before the latest image by a certain number of images (an example of an image captured before a latest image by a certain number of images among already captured images of an observation wavelength pattern) is displayed, only the images of the same wavelength pattern of the irradiation light $L_0$ as the wavelength pattern of the irradiation light $L_0$ of the selected observation mode are displayed. This thus makes observation using the display unit 18 easier.

Fourth Embodiment

In the endoscope system 10, the latest image among images of the same wavelength pattern as the wavelength pattern of the irradiation light $L_0$ of the selected observation mode, or an image captured before the latest image by a certain number of images is displayed at a display timing of a still image of a wavelength pattern that is different from the wavelength pattern of the irradiation light $L_0$ of the selected observation mode. Alternatively, an interpolation image may be displayed instead of the captured image.

Figure 8:
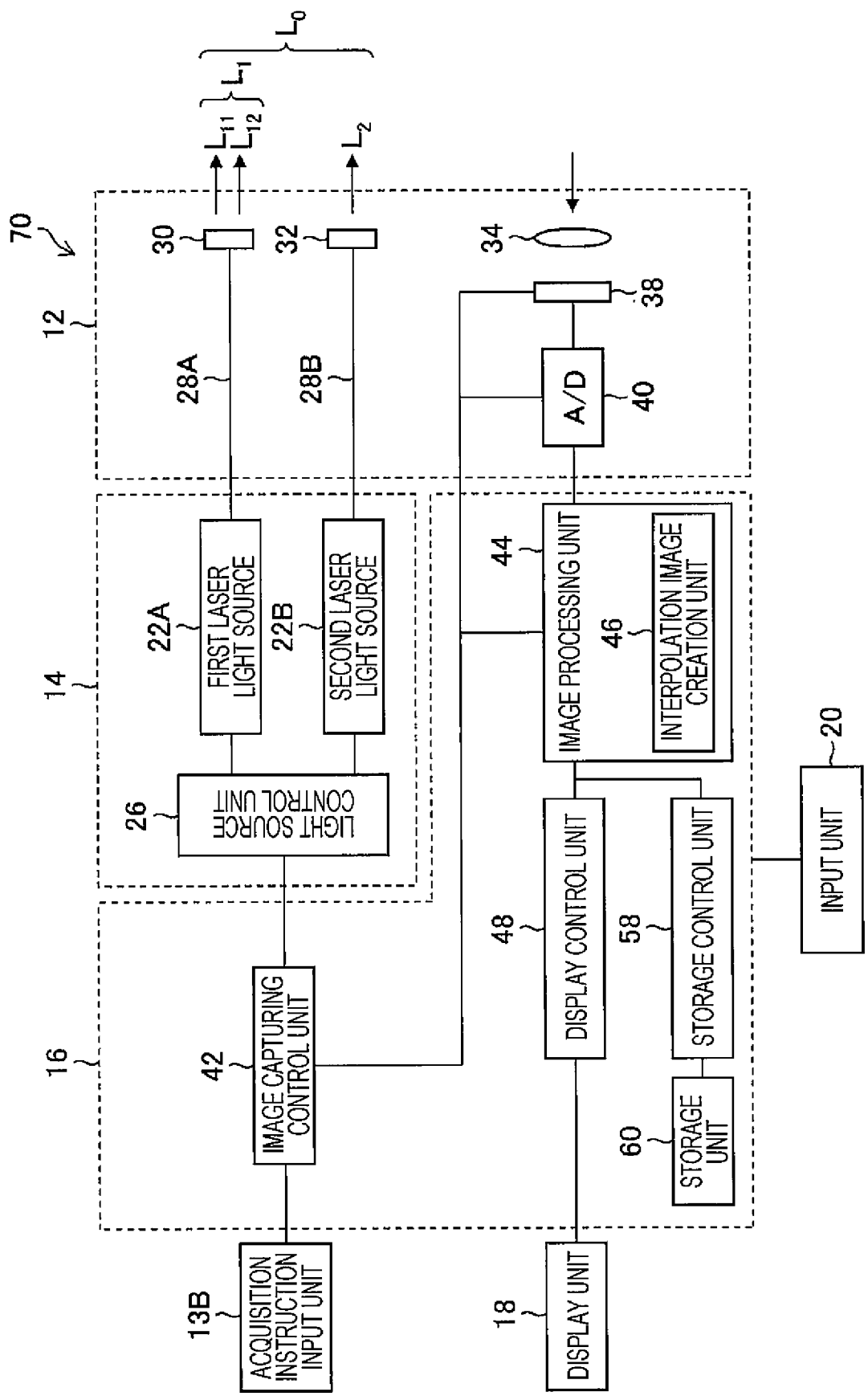
FIG. 8 is a block diagram illustrating functions of an endoscope system.

FIG. 8 is a block diagram illustrating functions of an endoscope system 70. Note that parts that are common to the block diagram illustrated in FIG. 2 are assigned the same reference signs, and detailed description thereof is omitted.

The endoscope system 70 includes an interpolation image creation unit 46 in the image processing unit 44. The interpolation image creation unit 46 includes a memory not illustrated, and creates an interpolation image from a plurality of images stored in the memory.

Figure 9:
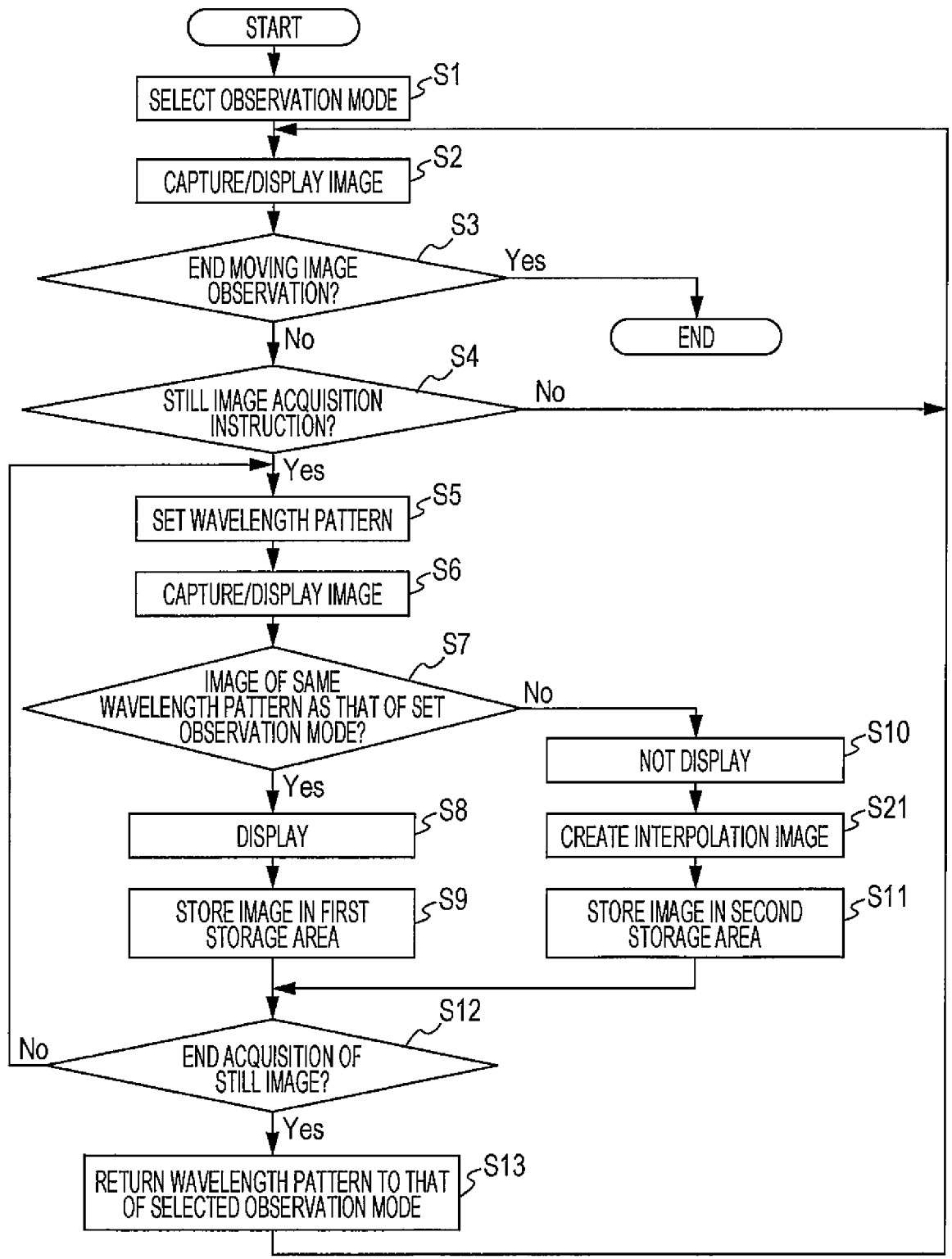
FIG. 9 is a flowchart illustrating a process of a training image collection method.
Figure 10:
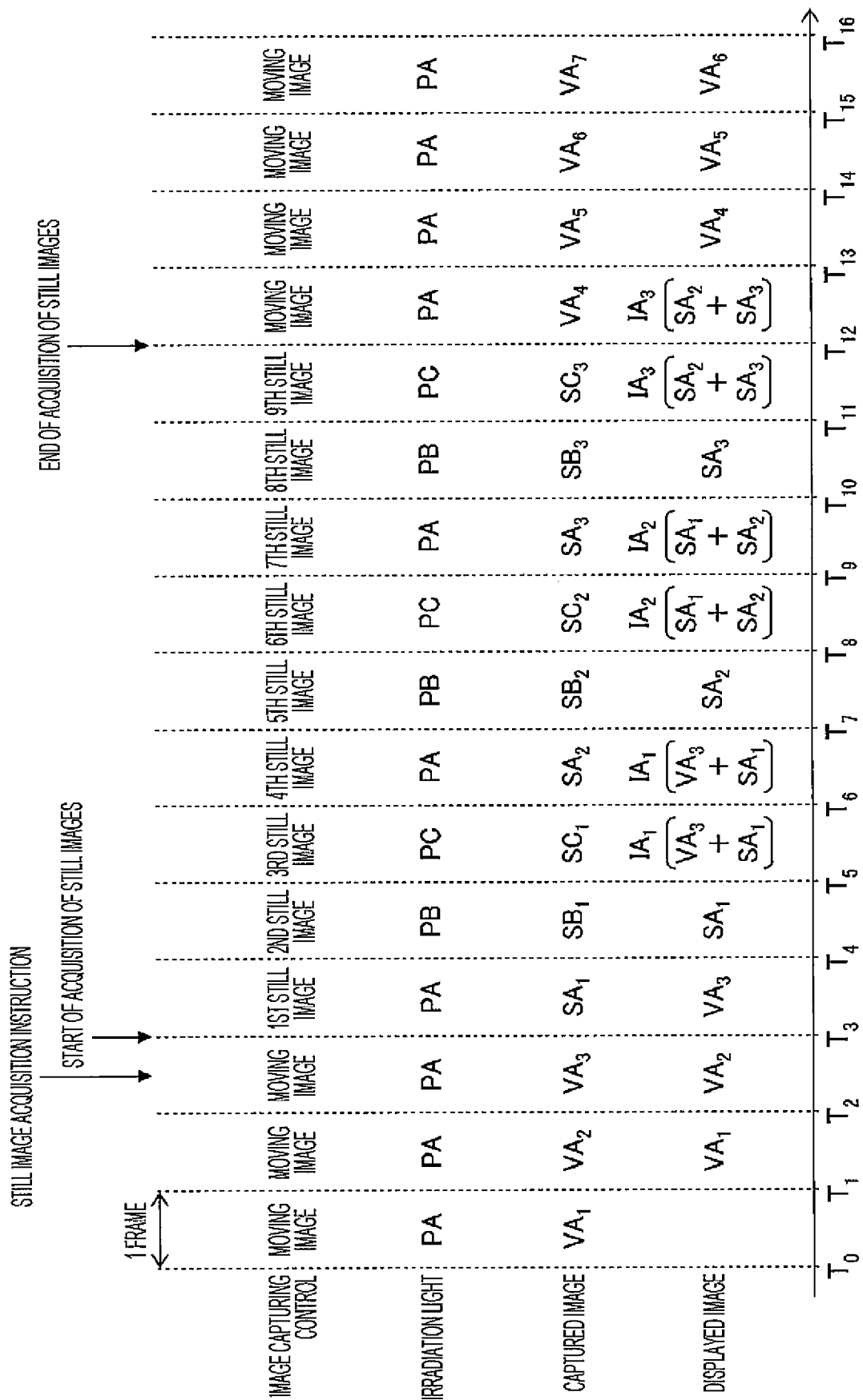
FIG. 10 is a timing chart describing the process of the training image collection method.

FIG. 9 is a flowchart illustrating a process of a training image collection method performed by the endoscope system 70. In addition, FIG. 10 is a timing chart describing the process of the training image collection method performed by the endoscope system 70. Note that parts that are common to the flowchart illustrated in FIG. 4 and to the timing chart illustrated in FIG. 5 are assigned the same reference signs, and detailed description thereof is omitted.

As in the first embodiment, a doctor selects the mode MA as an observation mode (step S1). The endoscope system 70 performs capturing of a moving image in the mode MA (step S2).

Note that it is assumed that nine still images are acquired by repeatedly performing three sets of processes, each set being a process of capturing one still image in the mode MA, capturing one still image in the mode MB, and capturing one still image in the mode MC, at the time of acquisition of still images.

If it is determined that a still image acquisition instruction is input in a period from time $T_2$ to time 13 (step S4), a still image acquisition process is started from time $T_3$. First, an image $SA_1$ is captured with the wavelength pattern PA in a period from time $T_3$ to time $T_4$. In addition, the image $VA_3$ is displayed on the display unit 18 (steps S5 and S6).

Since the image $SA_1$ captured at this time is an image of the same wavelength pattern as the wavelength pattern of the mode MA which is the selected observation mode, the image $SA_1$ is set as a to-be-displayed image (step S8).

An image $SB_1$ is captured with the wavelength pattern PB in a period from time $T_4$ to time $T_5$ which is the next image capturing timing.

Since the image $SB_1$ captured at this time is an image of the wavelength pattern that is different from the wavelength pattern of the mode MA, the image $SB_1$ is set not to be displayed (step S10).

In subsequent step S21, the interpolation image creation unit 46 creates an interpolation image interpolated between the latest image and an image captured before the latest image by a certain number of images, among images captured with the wavelength pattern of the irradiation light $L_0$ of the selected observation mode. Here, the interpolation image creation unit 46 creates an interpolation image $IA_1$ interpolated between the image $SA_1$ which is the latest image and an image $VA_3$ which is an image captured before the latest image $SA_1$ by one image. Note that the image $SA_1$ and the image $VA_3$ are stored in a memory (not illustrated) of the interpolation image creation unit 46.

The interpolation image $IA_1$ may be created by determining an average of each pixel of the image $SA_1$ and a corresponding pixel of the image $VA_3$ or by determining a weighted-average of each corresponding pair of pixels. In addition, the weight may be increased for a new image. Here, two images, i.e., the image $SA_1$ and the image $VA_3$, are used. An image captured before the image $SA_1$ by a certain number of images may further be used.

After the interpolation image $IA_1$ is created, the process proceeds to step S11. In step S11, the storage control unit 58 stores the image $SB_1$ in the second storage area of the storage unit 60 in association with information on the wavelength pattern PB of the irradiation light $L_0$ used in capturing of the image $SB_1$. The interpolation image $IA_1$ may be stored.

Subsequently, an image SCI is captured with the wavelength pattern PC in a period from time $T_5$ to time $T_6$. In addition, since the image $SB_1$ is set not to be displayed in previous step S10, the display control unit 48 does not display the image $SB_1$ on the display unit 18. Instead, the display control unit 48 displays the interpolation image $IA_1$ created in previous step S21 on the display unit 18 from time $T_5$ (steps S5 and S6).

Then the display control unit 48 sets the image $SC_1$ not to be displayed (step S10). Further, the interpolation image creation unit 46 creates an interpolation image $IA_1$ interpolated between the image $SA_1$ which is the latest image among images captured with the wavelength pattern of the irradiation light $L_0$ of the selected observation mode and the image $VA_3$ which is an image captured before the latest image by one image (step S21). Here, since the same interpolation image $IA_1$ has been created in previous step S21, the interpolation image $IA_1$ stored in the memory (not illustrated) of the interpolation image creation unit 46 can be used without performing any processing. Note that a new interpolation image may be created by changing the weight ratio used in weighted-averaging of the image $SA_1$ and the image $VA_3$.

An image $SA_2$ is captured with the wavelength pattern PA in a period from time $T_6$ to time $T_7$ which is the next image capturing timing. In addition, the display control unit 48 displays the interpolation image $IA_1$ created in previous step S21 on the display unit 18 (steps S5 and S6). This image $SA_2$ is set as a to-be-displayed image (step S8).

Further, an image $SB_2$ is captured with the wavelength pattern PB in a period from time $T_7$ to time $T_5$ which is the next image capturing timing. In addition, the display control unit 48 displays the image $SA_2$ captured the last time on the display unit 18 (steps S5 and S6).

Thereafter, in the similar manner, an interpolation image $IA_2$ created from the image $SA_1$ and the image $SA_2$ is displayed on the display unit 18 at display timings of the images $SB_2$ and $SC_2$ (from time $T_8$ to time $T_{10}$), and an interpolation image $IA_3$ created from the image $SA_2$ and the image $SA_3$ is displayed on the display unit 18 at display timings of the image $SB_3$ and the image $SC_3$ (from time $T_{11}$ to time $T_{13}$).

Here, an interpolation image is created from the latest image and an image captured before the latest image by a certain number of images. It is sufficient that an interpolation image is created from a plurality of images including the latest image among a plurality of images of the wavelength pattern of the selected observation mode or an image captured before the latest image by a certain number of images.

Such a display allows only images of the same wavelength pattern of the irradiation light $L_0$ as the wavelength pattern of the irradiation light $L_0$ of the selected observation mode to be displayed. This thus makes observation using the display unit 18 easier.

Fifth Embodiment

Acquisition of still images may be automatically performed independently of a still image acquisition instruction given by a doctor through the acquisition instruction input unit 13B.

Figure 11:
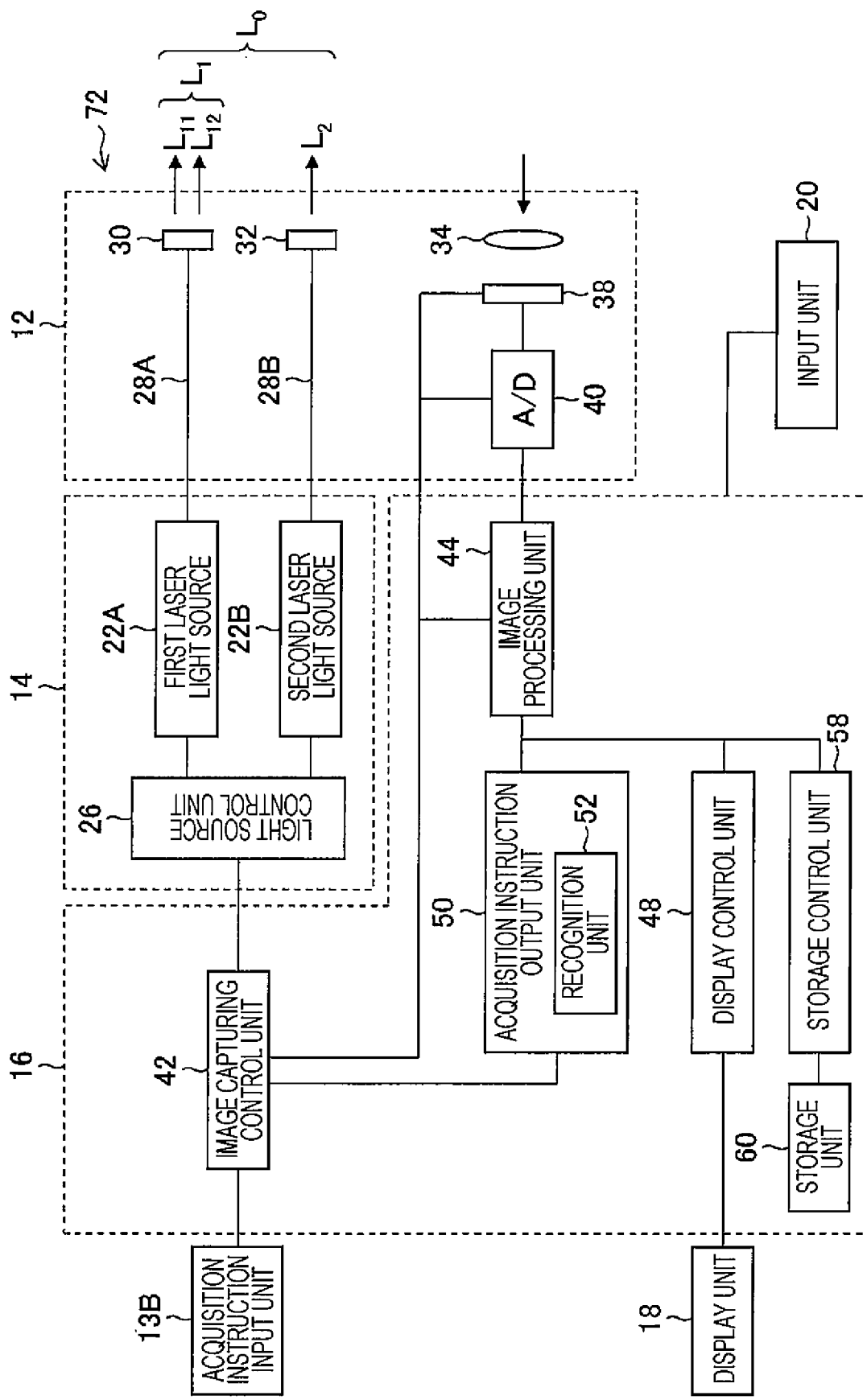
FIG. 11 is a block diagram illustrating functions of an endoscope system.

FIG. 11 is a block diagram illustrating functions of an endoscope system 72. Note that parts that are common to the block diagram illustrated in FIG. 2 are assigned the same reference signs, and detailed description thereof is omitted.

The processor device 16 of the endoscope system 72 includes an acquisition instruction output unit 50. The acquisition instruction output unit 50 automatically outputs a still image acquisition instruction. The still image acquisition instruction output by the acquisition instruction output unit 50 is input to the image capturing control unit 42.

The acquisition instruction output unit 50 includes a recognition unit 52. The recognition unit 52 detects a scene of interest from an input image. Here, the recognition unit 52 particularly detects a lesion region. Note that the scene of interest is not limited to a lesion region.

The recognition unit 52 can use a learning algorithm such as a neural network. In response to the recognition unit 52 detecting a lesion region, the acquisition instruction output unit 50 outputs a still image acquisition instruction.

Collection of training images performed by the endoscope system 72 will be described using a flowchart illustrated in FIG. 4.

First, a doctor selects an observation mode for capturing a moving image by using the input unit 20 (step S1). Subsequently, the endoscope system 72 captures a moving image in the selected observation mode (step S2).

The captured image is input to the acquisition instruction output unit 50 from the image processing unit 44. The recognition unit 52 of the acquisition instruction output unit 50 recognizes a lesion region from the input image. In response to the recognition unit 52 detecting a lesion region from the image, the acquisition instruction output unit 50 outputs a still image acquisition instruction. Consequently, YES is determined in step S4, and the process proceeds to step S5. The following processing is substantially the same as that described above.

The endoscope system 72 can automatically collect training images. In addition, only images of the wavelength pattern of the irradiation light $L_0$ that is the same as the wavelength pattern of the irradiation light $L_0$ of the selected observation mode are displayed. This thus makes observation using the display unit 18 easier.

Here, the recognition unit 52 detects a lesion region. In response to the recognition unit 52 detecting a lesion region, the acquisition instruction output unit 50 outputs a still image acquisition instruction. Alternatively, the acquisition instruction may be output in response to a trigger other than detection of a scene of interest, such as a lesion region. For example, a still image acquisition instruction may be output every certain period.

Sixth Embodiment

The endoscope system 10 stores all the captured still images in the storage unit 60. Alternatively, only images suitable for learning may be stored.

Figure 12:
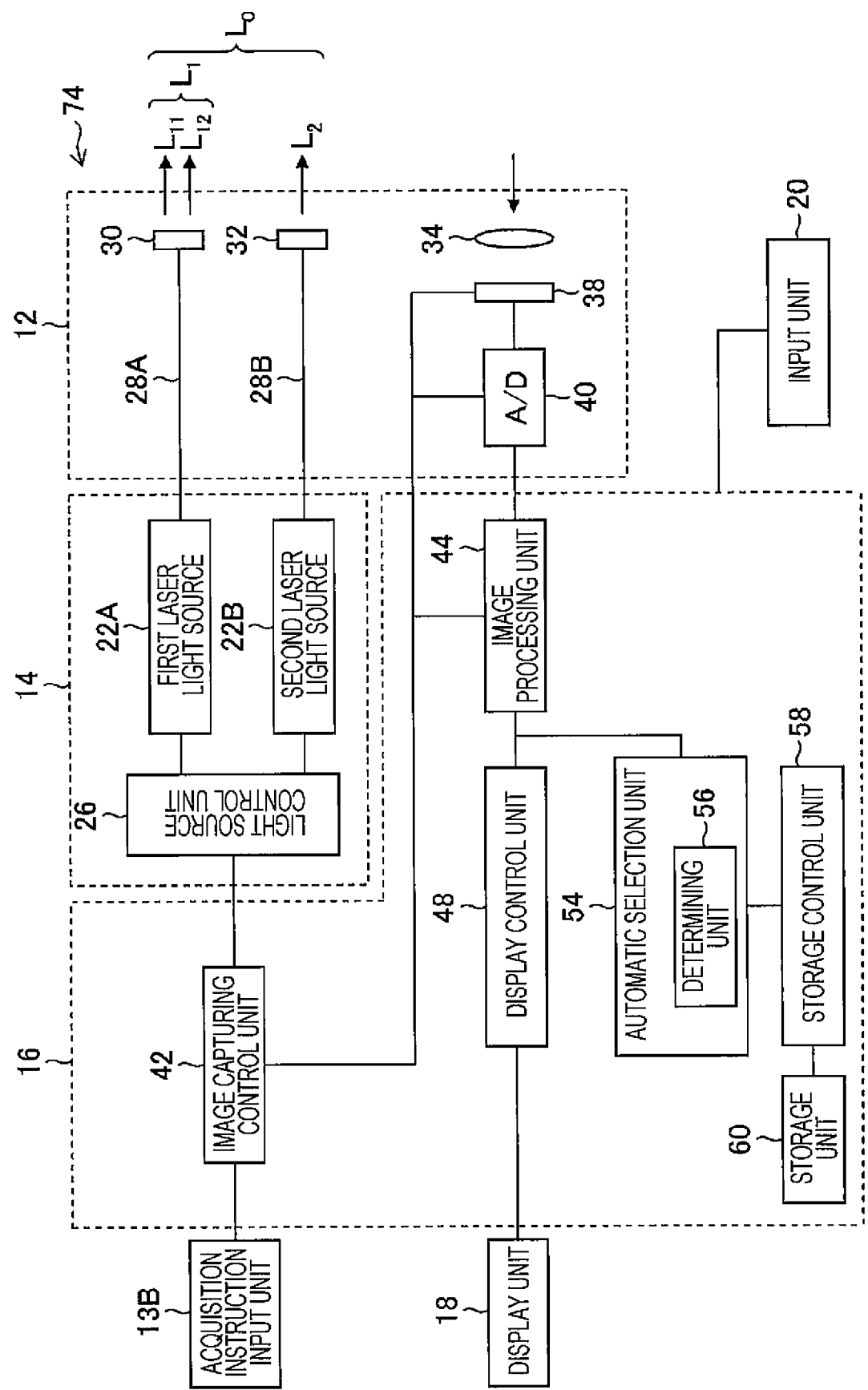
FIG. 12 is a block diagram illustrating functions of an endoscope system.

FIG. 12 is a block diagram illustrating functions of an endoscope system 74. Note that parts that are common to the block diagram illustrated in FIG. 2 are assigned the same reference signs, and detailed description thereof is omitted.

The processor device 16 of the endoscope system 74 includes an automatic selection unit 54. The automatic selection unit 54 automatically selects an image to be stored in a storage unit from among still images input thereto. The storage control unit 58 causes the still image selected by the automatic selection unit 54 to be stored in the storage unit 60.

The automatic selection unit 54 includes a determining unit 56. The determining unit 56 determines whether or not the input still image is suitable as a training image. Here, it is particularly determined whether or not the irradiation light $L_0$ used when the still image is captured has a desired wavelength pattern.

Figure 13:
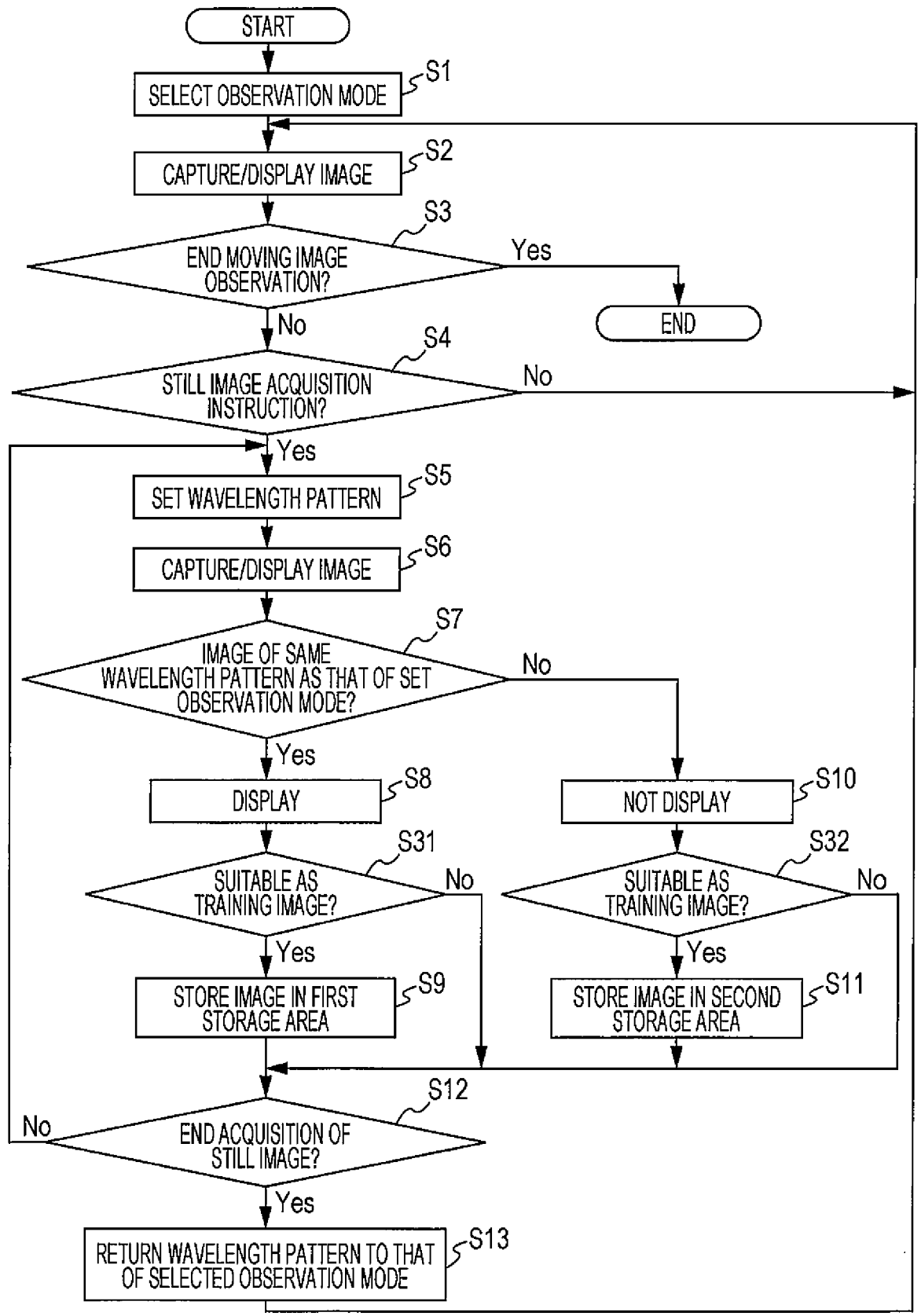
FIG. 13 is a flowchart illustrating a process of a training image collection method.

FIG. 13 is a flowchart illustrating a process of a training image collection method performed by the endoscope system 74. Note that parts that are common to the flowchart illustrated in FIG. 4 are assigned the same reference signs, and detailed description thereof is omitted.

In response to a still image acquisition instruction (step S4), the endoscope system 74 captures a still image (step S6). Subsequently, it is determined whether or not the image captured in step S6 is an image of the same wavelength pattern as the wavelength pattern of the selected observation mode (step S7).

If the image captured in step S6 is an image of the same wavelength pattern, the process proceeds to step S8. Then, the captured image is set as a to-be-displayed image (step S8).

In subsequent step S31, the determining unit 56 of the automatic selection unit 54 determines whether or not the captured image is suitable as a training image. Here, it is particularly determined whether or not the irradiation light $L_0$ used when the still image is captured has a desired wavelength pattern.

The determining unit 56 analyzes the color of the image to estimate the wavelength pattern of the irradiation light $L_0$ used in capturing of the image, and determines whether or not the estimated wavelength pattern is a desired wavelength pattern. If the determining unit 56 determines that the estimated wavelength pattern is a desired wavelength pattern, the automatic selection unit 54 selects the image as a training image. The process then proceeds to step S9.

In step S9, the image is stored in the first storage area of the storage unit 60 in association with information on the wavelength pattern.

In addition, if the determining unit 56 determines that the estimated wavelength pattern is not a desired wavelength pattern, the automatic selection unit 54 does not select the image as a training image and does not store the image. The process then proceeds to step S12.

On the other hand, if it is determined in step S7 that the captured image is not an image of the same wavelength pattern, the process proceeds to step S10. Then, the captured image is set not to be displayed (step S10).

In subsequent step S32, the determining unit 56 of the automatic selection unit 54 determines whether or not the captured image is suitable as a training image. As in step S31, it is particularly determined whether or not the irradiation light L used in capturing of the still image has a desired wavelength pattern.

Figure 6:
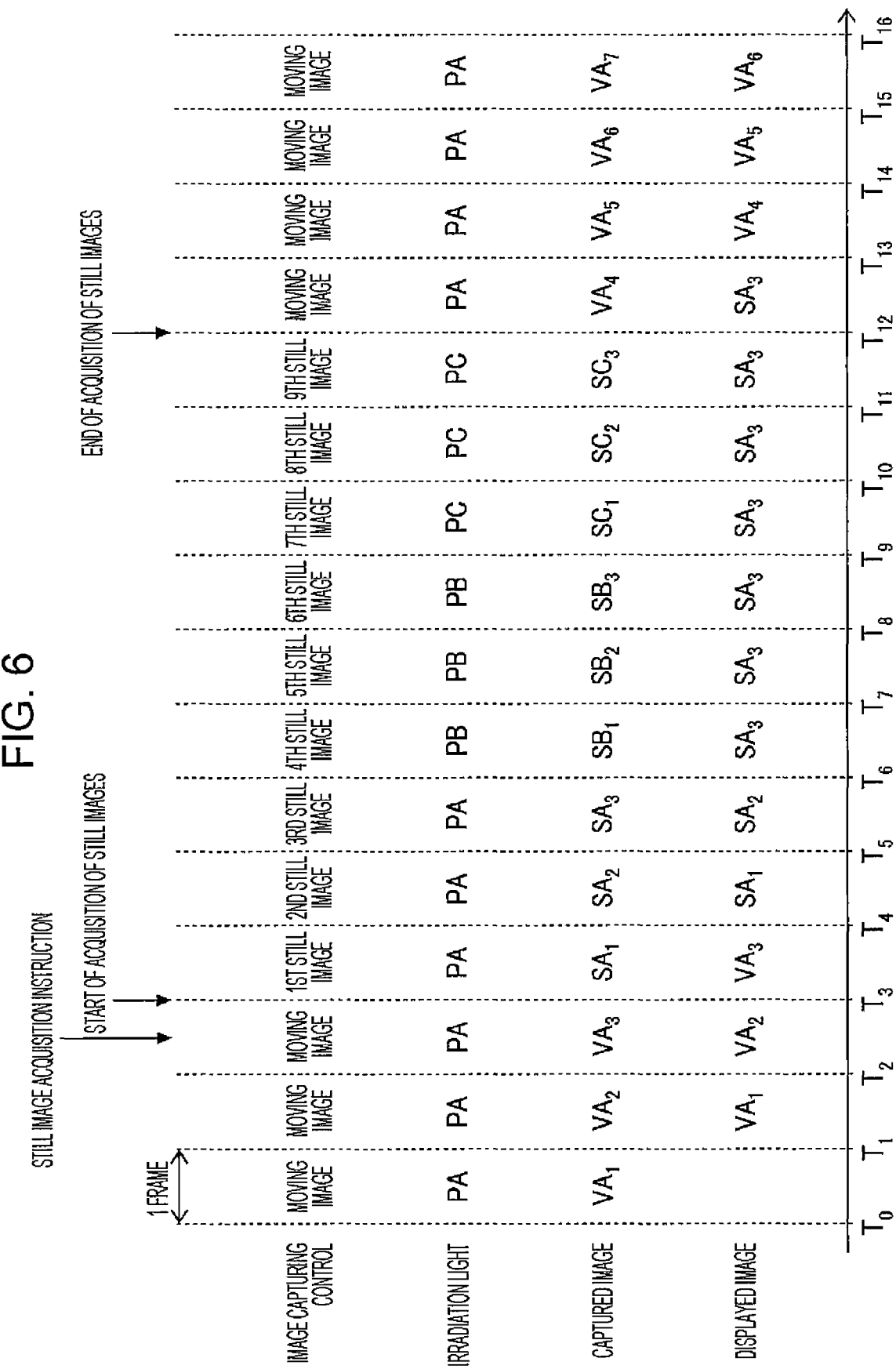
FIG. 6 is a timing chart describing the process of the training image collection method.

For example, in the case of the timing chart illustrated in FIG. 6, the irradiation light $L_0$ is changed from the wavelength pattern PA to the wavelength pattern PB at time $T_6$, and three images $SB_1$ to $SB_3$ are captured. Thus; the first image $SB_1$ is captured in a wavelength pattern transition state (an example of at the time of transition of the wavelength pattern), and the wavelength pattern of the irradiation light $L_0$ may not be a desired wavelength pattern.

The determining unit 56 analyzes the color of the image to estimate the wavelength pattern of the irradiation light $L_0$ used in capturing of the image, and determines whether or not the estimated wavelength pattern is a desired wavelength pattern. If the determining unit 56 determines that the estimated wavelength pattern is a desired wavelength pattern (an example of a result of determination), the automatic selection unit 54 selects the image as a training image. The process then proceeds to step S11.

In step S11, the image is stored in the second storage area of the storage unit 60 in association with information on the wavelength pattern.

In addition, if the determining unit 56 determines that the estimated wavelength pattern is not a desired wavelength pattern (an example of a result of determination), the automatic selection unit 54 does not select the image as a training image and does not store the image. The process then proceeds to step S12.

Note that the image that is displayed on the display unit 18 is similar to that described above.

The endoscope system 74 determines whether or not a captured still image is suitable as a training image and stores the suitable image. In this manner, the endoscope system 74 can collect preferable training images.

In addition, as in the case described above, since only images of the same wavelength pattern of the irradiation light $L_0$ as the wavelength pattern of the irradiation light $L_0$ of the selected observation mode are displayed, the display color during acquisition of still images is the same display color during capturing of a moving image, that is, becomes constant. This thus makes observation using the display unit 18 easier.

Here, it is determined that an image for which the irradiation light $L_0$ used in capturing of the still image does not have a desired wavelength pattern is not suitable as a training image. However, the determination criterion is not limited to this. For example, it may be determined that an image in which blurring has occurred, an out-of-focus image, an captured with a lens having a spray of water or dust thereon, or the like is not suitable as a training image. In addition, the most suitable image may be determined from among images that are suitable as training images, and only the determined image may be stored.

In addition, the acquired still images may be displayed on the display unit 18, and a doctor may select an image to be stored in the storage unit 60 as a training image from among the displayed images by using the input unit 20 (an example of a to-be-storage image selection unit). In addition, instead of displaying all the acquired still images on the display unit 18, only still images determined to be suitable as training images by the determining unit 56 may be displayed on the display unit 18.

Seventh Embodiment

The endoscope system 10 changes a light-quantity ratio between a plurality of light sources to change the wavelength pattern of the irradiation light $L_0$. Alternatively, a light source to be turned on among the plurality of light sources may be selected to change the wavelength pattern of the irradiation light.

FIG. 14 is a block diagram illustrating functions of an endoscope system 76. Note that parts that are common to the block diagram illustrated in FIG. 2 are assigned the same reference signs, and detailed description thereof is omitted.

The light source device 14 of the endoscope system 76 includes a first light source 24A, a second light source 24B, and a third light source 24C.

The light source control unit 26 selects one light source from among the first light source 24A, the second light source 24B, and the third light source 24C, and turns on the selected light source and turns off the other light sources. The diffusion member 32 is irradiated with light emitted from the light source that is turned on through the optical fiber 28B. The light outgoing from the diffusion member 32 serves as the irradiation light $L_0$ of the endoscope system 76.

Here, using the first light source 24A as a light source having a wavelength pattern of the wavelength pattern PA, the second light source 24B as a light source having a wavelength pattern of the wavelength pattern PB and the third light source 24C as a light source having a wavelength pattern of the wavelength pattern PC, still images irradiated with the irradiation light $L_0$ of the respective wavelength patterns can be acquired.

As the first light source 24A, the second light source 24B, and the third light source 24C, semiconductor light sources such as LEDs (Light Emitting Diodes) as well as combinations of a laser diode and a fluorescent body can be used.

Eighth Embodiment

The example of changing the wavelength pattern of the irradiation light $L_0$ with which a part to be observed is irradiated has been described above. Alternatively, the wavelength pattern of the irradiation light $L_0$ may be kept constant and a wavelength pattern of returning light received by the imaging element 38 may be changed.

FIG. 15 is a block diagram illustrating functions of an endoscope system 78. Note that parts that are common to the block diagram illustrated in FIG. 2 are assigned the same reference signs, and detailed description thereof is omitted.

The endoscope 12 of the endoscope system 78 includes a filter group 36 (an example of a wavelength pattern changing unit) having a plurality of filters. Different filters of the plurality of filters limit different wavelength ranges of light transmitting therethrough. The filter group 36 is disposed between the imaging lens 34 and the imaging element 38 in the optical path of the returning light. For example, the filter group 36 can be configured as a rotational filter turret.

The light source control unit 26 sets a light-quantity ratio between the light emitted from the first laser light source 22A and the light emitted from the second laser light source 22B to be constant. In addition, the image capturing control unit 42 (an example of a wavelength pattern changing unit) controls the filter group 36 to insert a necessary filter to or evacuate a necessary filter from the optical path. In this manner, the image capturing control unit 42 changes the wavelength pattern of the returning light received by the imaging element 38.

For example, the filter group 36 includes three filters, that is, a filter that makes transmitting light have a wavelength pattern of the wavelength pattern PA, a filter that makes transmitting light have a wavelength pattern of the wavelength pattern PB, and a filter that makes transmitting light have a wavelength pattern of the wavelength pattern PC. One filter among the three filters is inserted to the optical path. In this manner, images of the respective wavelength patterns can be captured.

Note that the image that is displayed on the display unit 18 is similar to that described above.

The endoscope system 78 sequentially captures images of a plurality of wavelength patterns different from one another. In this manner, the endoscope system 78 can appropriately collect training images.

In addition, as in the case described above, since only images of the same wavelength pattern of the irradiation light $L_0$ as the wavelength pattern of the irradiation light $L_0$ of the selected observation mode are displayed, the display color during acquisition of still images is the same display color during capturing of a moving image, that is, becomes constant. This thus makes observation using the display unit 18 easier.

In the endoscope systems 10, 70, 72, 74, 76, and 78, a still image captured with the same wavelength pattern as that of the observation mode is stored in the first storage area as a diagnosis image. Alternatively, the diagnosis image may be stored in the second storage area. In this manner, still images captured with the same wavelength pattern as that of the observation mode can be collected as training images.

Appendices

In addition to the embodiments and examples described above, configurations described below are also within the scope of the present invention.

(Appendix 1) A medical image processing apparatus wherein
a medical image analysis processing unit detects a region of interest on the basis of a feature quantity of pixels of a medical image, the region of interest being a region to be focused on, and
a medical image analysis result acquisition unit acquires a result of an analysis performed by the medical image analysis processing unit.

(Appendix 2) A medical image processing apparatus wherein
a medical image analysis processing unit detects presence or absence of a target of interest on the basis of a feature quantity of pixels of a medical image, and
a medical image analysis result acquisition unit acquires a result of an analysis performed by the medical image analysis processing unit.

(Appendix 3) The medical image processing apparatus wherein
the medical image analysis result acquisition unit
acquires the result of the analysis of the medical image from a recording apparatus, and
the result of the analysis is either the region of interest which is a region to be focused on included in the medical image or the presence or absence of the target of interest, or is both the region of interest and the presence or absence.

(Appendix 4) The medical image processing apparatus wherein the medical image is an ordinary light image obtained by radiating light of a white range or by radiating light of a plurality of wavelength ranges as the light of the white range.

(Appendix 5) The medical image processing apparatus wherein the medical image is an image obtained by radiating light of a particular wavelength range, and the particular wavelength range is a range narrower than a white wavelength range.

(Appendix 6) The medical image processing apparatus wherein the particular wavelength range is a visible wavelength range of blue or green.

(Appendix 7) The medical image processing apparatus wherein the particular wavelength range includes a wavelength range that is greater than or equal to 390 nm and is less than or equal to 450 nm, or is greater than or equal to 530 nm and is less than or equal to 550 nm, and light of the particular wavelength range has a peak wavelength in the wavelength range that is greater than or equal to 390 nm and is less than or equal to 450 nm, or is greater than or equal to 530 nm and is less than or equal to 550 nm.

(Appendix 8) The medical image processing apparatus wherein the particular wavelength range is a visible wavelength range of red.

(Appendix 9) The medical image processing apparatus wherein the particular wavelength range includes a wavelength range that is greater than or equal to 585 nm and is less than or equal to 615 nm, or is greater than or equal to 610 nm and is less than or equal to 730 nm, and light of the particular wavelength range has a peak wavelength in the wavelength range that is greater than or equal to 585 nm and is less than or equal to 615 nm, or is greater than or equal to 610 nm and is less than or equal to 730 nm.

(Appendix 10) The medical image processing apparatus wherein the particular wavelength range includes a wavelength range in which a light absorption coefficient differs between oxyhemoglobin and deoxyhemoglobin, and light of the particular wavelength range has a peak wavelength in the wavelength range in which the light absorption coefficient differs between oxyhemoglobin and deoxyhemoglobin.

(Appendix 11) The medical image processing apparatus wherein the particular wavelength range includes a wavelength range of 400±10 nm, 440±10 nm, or 470±10 nm, or a wavelength range that is greater than or equal to 600 nm and is less than or equal to 750 nm, and light of the particular wavelength range has a peak wavelength in the wavelength range of 400±10 nm, 440±10 nm, or 470±10 nm, or in the wavelength range that is greater than or equal to 600 nm and is less than or equal to 750 nm.

(Appendix 12) The medical image processing apparatus wherein the medical image is an inside body image of an inside of a body, and the inside body image has information of fluorescent light emitted by a fluorescence substance in the body.

(Appendix 13) The medical image processing apparatus wherein the fluorescent light is obtained by irradiating the inside of the body with excitation light having a peak that is greater than or equal to 390 nm and is less than or equal to 470 nm.

(Appendix 14) The medical image processing apparatus wherein the medical image is an inside body image of an inside of a body, and the particular wavelength range is a wavelength range of infrared light.

(Appendix 15) The medical image processing apparatus wherein the particular wavelength range includes a wavelength range that is greater than or equal to 790 nm and is less than or equal to 820 nm, or is greater than or equal to 905 nm and is less than or equal to 970 nm, and light of the particular wavelength range has a peak wavelength in the wavelength range that is greater than or equal to 790 nm and is less than or equal to 820 nm, or is greater than or equal to 905 nm and is less than or equal to 970 nm.

(Appendix 16) The medical image processing apparatus wherein a medical image acquisition unit includes a special light image acquisition unit that acquires a special light image having information on the particular wavelength range on the basis of an ordinary light image that is obtained by radiating light of a white range or light of a plurality of wavelength range as the light of the white range, and the medical image is the special light image.

(Appendix 17) The medical image processing apparatus wherein a signal of the special wavelength range is obtained through a calculation based on color information of RGB (Red, Green, and Blue) or of CMY (Cyan, Magenta, and Yellow) included in the ordinary light image.

(Appendix 18) The medical image processing apparatus including a feature quantity generation unit that generates a feature quantity image through a calculation based on at least one of the ordinary light image that is obtained by radiating light of a white range or light of a plurality of wavelength ranges as the light of the white range and the special light image obtained by radiating light of the particular wavelength range, wherein the medical image is the feature quantity image.

(Appendix 19) An endoscope apparatus including:

the medical image processing apparatus according to any one of appendices 1 to 18; and an endoscope that acquires an image by radiating at least either light of a white wavelength range or light of a particular wavelength range.

(Appendix 20) A diagnosis assistant apparatus including: the medical image processing apparatus according to any one of appendices 1 to 18.

(Appendix 21) A medical work assistant apparatus including: the medical image processing apparatus according to any one of appendices 1 to 18.

<Others>

As the wavelength pattern, white light, BLI, BLI-bright (registered trademark), a particular single wavelength, any combination of a plurality of wavelengths, or the like can be used.

Collection of training images has been described herein, images to be collected are not limited to training images of a learning algorithm. For example, images to be collected may be test images for use in evaluation of the performance of an endoscope system, images for use in a study of how differently a part to be observed is viewed depending on the wavelength of the irradiation light, or the like.

The recognition method described above may be configured as a program causing a computer to implement individual steps, and may be configured as a non-transitory recording medium such as a CD-ROM (Compact Disk-Read Only Memory) storing this program.

In the embodiments described above, for example, a hardware structure of a processing unit that executes various processes of the processor device 16 is, for example, various processors cited below. The various processors include a CPU (Central Processing Unit) which is a general-purpose processor that executes software (program) to function as various processing units, a GPU (Graphics Processing Unit) which is a processor specialized for image processing, a PLD (Programmable Logic Device), such as an FPGA (Field Programmable Gate Array), which is a processor whose circuitry is changeable after production, a dedicated electric circuit, such as an ASIC (Application Specific Integrated Circuit), which is a processor having circuitry designed specifically for executing specific processing, and the like.

One processing unit may be constituted by one of these various processors, or by two or more processors of the same kind or different kinds (for example, a plurality of FPGAs, a combination of a CPU and an FPGA, or a combination of a CPU and a GPU). In addition, a plurality of processing units may be constituted by one processor. Examples in which a plurality of processing unit are constituted by one processor include a first configuration, as exemplified by computers such as a server and a client, in which a combination of one or more CPUs and software constitutes one processor and this processor functions as a plurality of processing units. The examples also include a second configuration, as exemplified by a SoC (System On Chip) or the like, in which a processor that implements functions of the entire system including a plurality of processing units on a single IC (Integrated Circuit) chip is used. As described above, the various processing units are configured using one or more of the various processors in terms of hardware structure.

Further, the hardware structure of these various processors is, more specifically, electric circuitry in which circuit elements such as semiconductor elements are combined.

The technical scope of the present invention is not limited to the scope described in the embodiments above. The configurations or the like in each of the respective embodiments can be appropriately combined within a range not departing from the gist of the present invention.

Reference Signs List 10 endoscope system
12 endoscope
12A insertion part
12B operation unit
12C bending part
12D tip part
12E angle knob
13A mode switch
13B acquisition instruction input unit
14 light source device
16 processor device
18 display unit
20 input unit
22A first laser light source
22B second laser light source
24A first light source
24B second light source
24C third light source
26 light source control unit
28A optical fiber
28B optical fiber
30 fluorescent body
32 diffusion member
34 imaging lens
36 filter group
38 imaging element
40 analog-to-digital converter
42 image capturing control unit
44 image processing unit
46 interpolation image creation unit
48 display control unit
50 acquisition instruction output unit
52 recognition unit
54 automatic selection unit
56 determining unit
58 storage control unit
60 storage unit
70 endoscope system
72 endoscope system
74 endoscope system
76 endoscope system
78 endoscope system
$IA_1$ to $IA_3$ interpolation image
$SA_1$ to $SA_3$ image
$SB_1$ to $SB_3$ image
$SC_1$ to $SC_3$ image
$L_0$ irradiation light
$L_1$ light
$L_{11}$ excitation light
$L_{12}$ laser light
$L_2$ light
S1 to S32 processing step of training image collection

What is claimed is:

1. An endoscopic image acquisition system comprising:
a light source that irradiates a part to be observed in a body cavity of a patient with irradiation light;
image sensor that receives returning light from the part to be observed and captures images of the part to be observed;
a processor configured to:
cause the captured images to be sequentially displayed on a display device;
change a wavelength pattern of the irradiation light or the returning light;
accept an acquisition instruction to acquire images;
cause images to be captured at a certain frame rate by using an observation wavelength pattern and cause images to be sequentially captured by using a plurality of wavelength patterns different from one another in response to acceptance of the acquisition instruction, wherein the observation wavelength pattern is selected from the plurality of wavelength patterns; and
cause the images sequentially captured by using the plurality of wavelength patterns different from one another to be stored in a storage device, wherein
the processor causes the images captured at the certain frame rate by using the observation wavelength pattern to be displayed on the display device, and sets an image captured by using a wavelength pattern other than the observation wavelength pattern among the images sequentially captured by using the plurality of wavelength patterns not to be displayed when receiving the acquisition instruction.

2. The endoscopic image acquisition system according to claim 1, wherein the processor displays a latest image among already captured images of the observation wavelength pattern or an image captured before the latest image by a certain number of images, instead of displaying an image of a wavelength pattern other than the observation wavelength pattern.

3. The endoscopic image acquisition system according to claim 1, wherein
the processor further creates an interpolation image from a plurality of images including a latest image among captured images of the observation wavelength pattern or an image captured before the latest image by a certain number of images, wherein
the processor displays the interpolation image instead of displaying an image of a wavelength pattern other than the observation wavelength pattern.

4. The endoscopic image acquisition system according to claim 1, wherein
the light source comprises a plurality of light sources, and
the processor selects a light source to be turned on from among the plurality of light sources to change the wavelength pattern of the irradiation light.

5. The endoscopic image acquisition system according to claim 1, wherein
the light source comprises a plurality of light sources, and
the processor changes a ratio between light quantities of the plurality of light sources to change the wavelength pattern of the irradiation light.

6. The endoscopic image acquisition system according to claim 1, wherein
the image sensor comprises a filter that limits a wavelength range of light transmitting through the filter, and
the processor controls the filter to change the wavelength pattern of the returning light.

7. The endoscopic image acquisition system according to claim 1, wherein
the images of the plurality of wavelength patterns different from one another include an image of the observation wavelength pattern, and
the processor causes the image of the observation wavelength pattern to be stored in a first storage area of the storage device, and causes an image of a wavelength pattern other than the observation wavelength pattern to be stored in a second storage area of the storage device, the second storage area being different from the first storage area.

8. The endoscopic image acquisition system according to claim 1, wherein the processor causes the image to be stored in the storage device in association with information on the wavelength pattern used in capturing of the image.

9. The endoscopic image acquisition system according to claim 1, wherein
the processor further allows a user to select the observation wavelength pattern, wherein
the processor causes images to be captured with the selected wavelength pattern at a certain frame rate.

10. The endoscopic image acquisition system according to claim 1, wherein
the processor further allows a user to select an order of the plurality of wavelength patterns used in sequential capturing of the images of the plurality of wavelength patterns different from one another, wherein
the processor causes the images of the plurality of wavelength patterns different from one another to be sequentially captured in the selected order.

11. The endoscopic image acquisition system according to claim 1, wherein
the processor further allows a user to select an image to be stored in the storage device from among the images of the plurality of wavelength patterns different from one another, wherein
the processor causes the selected image to be stored in the storage device.

12. The endoscopic image acquisition system according to claim 1, wherein
the processor further automatically selects an image to be stored in the storage device from among the images of the plurality of wavelength patterns different from one another, wherein
the processor causes the automatically selected image to be stored in the storage device.

13. The endoscopic image acquisition system according to claim 12, wherein
the processor further determines an image captured at the time of transition of the wavelength pattern when the images of the plurality of wavelength patterns different from one another are sequentially captured, wherein
the processor automatically selects the image based on a result of the determination.

14. The endoscopic image acquisition system according to claim 1, further comprising
an interface with which a user inputs the acquisition instruction, wherein
the processor accepts the acquisition instruction from the interface.

15. The endoscopic image acquisition system according to claim 1, wherein
the processor further recognizes a scene of interest from among the captured images; and
outputs the acquisition instruction in response to recognizing the scene of interest.

16. An endoscopic image acquisition method comprising:
an irradiation step of irradiating a part to be observed in a body cavity of a patient with irradiation light;
an image capturing step of receiving returning light from the part to be observed and capturing images of the part to be observed;
a display control step of causing the captured images to be sequentially displayed on a display device;
a wavelength pattern changing step of changing a wavelength pattern of the irradiation light or the returning light;
an accepting step of accepting an acquisition instruction to acquire images;
an image capturing control step of causing images to be captured at a certain frame rate by using an observation wavelength pattern and causing images to be sequentially captured by using a plurality of wavelength patterns different from one another in response to acceptance of the acquisition instruction, wherein the observation wavelength pattern is selected from the plurality of wavelength patterns; and
a storage control step of causing the images sequentially captured by using the plurality of wavelength patterns different from one another to be stored in a storage device, wherein the display control step causes the images captured at the certain frame rate by using the observation wavelength pattern to be displayed on the display device, and sets an image captured by using a wavelength pattern other than the observation wavelength pattern among the images sequentially captured by using the plurality of wavelength patterns not to be displayed when receiving the acquisition instruction.

* * * * *